United States Patent
Wu et al.

(10) Patent No.: US 8,728,487 B2
(45) Date of Patent: May 20, 2014

(54) ATTENUATED LIVE VACCINE FOR PREVENTION OF PORCINE REPRODUCTIVE AND RESPIRATORY SYNDROME

(75) Inventors: Hua Wu, Beijing (CN); Xue Leng, Jilin (CN); Zhenguang Li, Jilin (CN); Fengxue Wang, Beijing (CN)

(73) Assignee: Hua Wu, Chaoyang District Beijing (CN)

( * ) Notice: Subject to any disclaimer, the term of this patent is extended or adjusted under 35 U.S.C. 154(b) by 638 days.

(21) Appl. No.: 13/009,866

(22) Filed: Jan. 20, 2011

(65) Prior Publication Data

US 2012/0189655 A1    Jul. 26, 2012

(51) Int. Cl.
| | |
|---|---|
| *A61K 39/12* | (2006.01) |
| *C07H 21/00* | (2006.01) |
| *C12N 15/85* | (2006.01) |
| *A61P 37/04* | (2006.01) |
| *C12Q 1/70* | (2006.01) |
| *A61P 31/14* | (2006.01) |
| *C12N 5/10* | (2006.01) |
| *C12N 7/04* | (2006.01) |

(52) U.S. Cl.
USPC ...... 424/204.1; 435/5; 435/235.1; 435/320.1; 536/23.72

(58) Field of Classification Search
None
See application file for complete search history.

(56) References Cited

U.S. PATENT DOCUMENTS

| | | | |
|---|---|---|---|
| 2003/0064074 A1* | 4/2003 | Chang et al. | 424/184.1 |
| 2010/0215694 A1 | 8/2010 | Calvert et al. | |
| 2010/0267929 A1 | 10/2010 | Faaberg et al. | |
| 2012/0189655 A1* | 7/2012 | Wu et al. | 424/204.1 |

FOREIGN PATENT DOCUMENTS

CN        101633909 A        1/2010

OTHER PUBLICATIONS

Wang et al. (Research in Veterinary Science. 2013; 95: 1-7).*
Kim et al, "Insertion and deletion in a non-essential region of the nonstructural protein 2 (nsp2) of porcine reproductive and respiratory syndrome (PRRS) virus: effects on virulence and immunogenicity", Virus Genes, 38: 118-128; published online on Dec. 2, 2008.
Han et al, "Identification of Nonessential Regions of the nsp2 Replicase Protein of Porcine Reproductive and Respiratory Syndrome Virus Strain VR-2332 for Replication in Cell Culture", Journal of Virology, 81(18): 9878-9890; published ahead of print on May 23, 2007.
Zhou et al, "The 30-Amino-Acid Deletion in the Nsp2 of Highly Pathogenic Porcine Reproductive and Respiratory Syndrome Virus Emerging in China Is Not Related to Its Virulence", Journal of Virology, 83(10): 5156-5167; Published ahead of print on Feb. 25, 2009.

* cited by examiner

*Primary Examiner* — Shanon A Foley
(74) *Attorney, Agent, or Firm* — Jun He Law Offices P.C.; James J. Zhu

(57) ABSTRACT

The present disclosure provides an attenuated live vaccine strain and the formulations thereof, for preventing pigs from infection of porcine reproductive and respiratory syndrome (PRRS). The preparation methods for the vaccines and the formulations are also provided. The attenuated live vaccine strain provided herein offers significant immunological protection to pigs against PRRS. The vaccine formulations of the present disclosure also have advantages in long shelf lives as well as good stability during storage.

17 Claims, 1 Drawing Sheet

SEQUENCE LISTING

<160> NUMBER OF SEQ ID NOS: 7

<210> SEQ ID NO 1
<211> LENGTH: 14966
<212> TYPE: DNA
<213> ORGANISM: Porcine reproductive and respiratory syndrome virus

<400> SEQUENCE: 1

| | | | | | | |
|---|---|---|---|---|---|---|
| atgacgtata | ggtgttggct | ctatgccacg | gcatttgtat | tgtcaggagc | tgtgaccata | 60 |
| ggcacagccc | aaaacttgct | gcacgggaac | accctcctgt | gacagccctc | ttcaggggga | 120 |
| ttaggggtct | gtccctaaca | ccttgcttcc | ggagttgcac | tgctttacgg | tctctccacc | 180 |
| cctttaacca | tgtctgggat | acttgatcgg | tgcacgtgta | ccccaatgc | cagggtgttt | 240 |
| gtggcggagg | gccaggtcta | ctgcacacga | tgtctcagtg | cacggtctct | ccttcctctg | 300 |
| aatctccaag | ttcctgagct | tggggtgctg | ggtctattct | ataggcccga | agagccactc | 360 |
| cggtggacgt | tgccacgtgc | attccccact | gtcgagtgct | ccccgccgg | ggcctgctgg | 420 |
| ctttctgcga | tctttccgat | tgcacgaatg | actagtggaa | acctgaactt | caacaaaga | 480 |
| atggtgcggg | tcgcagctga | aatctacaga | gccggccaac | tcacccctac | agttctaaag | 540 |
| actctacaag | tttatgaacg | gggttgtcgc | tggtacccca | ttgtcgggcc | cgtccctggg | 600 |
| gtgggcgttt | acgccaactc | cctgcatgtg | agtgacaaac | ctttcccggg | agcaactcat | 660 |
| gtgttaacca | acttgccgct | cccgcagagg | cccaaacctg | aggacttttg | ccctttgag | 720 |
| tgtgctatgg | ctgacgtcta | tgacattggt | cgtggcgccg | tcatgtatgt | ggccggagga | 780 |
| aaggtctctt | gggcccctcg | tggtgggaat | gaagtgaaat | tgaacctgt | ccccaaggag | 840 |
| ttgaagttgg | ttgcgaaccg | actccacacc | tccttcccgc | cccatcacgt | agtggacatg | 900 |
| tccaggttta | ccttcatgac | ccctgggagt | ggtgtctcca | tgcgggttga | gtaccaatac | 960 |
| ggctgcctcc | ccgctgacac | tgtccctgaa | ggaaactgct | ggtggcgctt | gtttgactcg | 1020 |
| ctcccaccgg | aagttcagta | caaagaaatt | cgccacgcta | accaatttgg | ctatcaaacc | 1080 |
| aagcatggtg | tccctggcaa | gtacctacag | cggaggctgc | aagttaatgg | tcttcggaca | 1140 |
| gtgaccgaca | cacatggacc | tatcgtcata | cagtacttct | ctgttaagga | gagttggatc | 1200 |
| cgccacctga | agttggtgga | agaacccagc | ctccccgggt | tgaggatct | cctcagaatc | 1260 |
| agggttgagc | ccaatacgtc | accactggct | ggaaaggatg | agaagatttt | ccggtttggc | 1320 |
| agtcataagt | ggtacggtgc | cggaaagaga | gcaaggaaaa | cacgctctgg | tgcgactact | 1380 |
| atggtcgctc | atcacgcttc | gtccgctcat | aaaatccggc | aggccacgaa | gcacgagggt | 1440 |
| gccggcgcta | acaaggctga | gcatctcaag | cgctactctc | cgcctgccga | agggaactgt | 1500 |
| ggttggcact | gcatttccgc | catcgccaac | cggatggtga | attccaactt | gagaccacc | 1560 |
| cttcctgaaa | gagtaaggcc | ttcagatgac | tgggccactg | acgaggatct | tgtgaatacc | 1620 |
| atccaaatcc | tcaggctccc | tgcggccttg | gacaggaacg | gcgcttgcgg | tagcgccaag | 1680 |
| tacgtgctta | aactggaggg | tgagcattgg | actgtctctg | tgatccctgg | gatgtcccct | 1740 |
| actttgctcc | cccttgaatg | tgttcagggt | tgttgtgaac | ataagggcgg | tcttgtttcc | 1800 |
| ccggatgcgg | tcgaaatttc | cggatttgat | cctgcctgcc | ttgaccgact | ggctaaggta | 1860 |
| atgcacttgc | ctagcagtac | catcccagcc | gctctggccg | aattgtccga | cgactccaac | 1920 |
| cgtccggttt | cccggccgc | tactacgtgg | actgtttcgc | aattctatgc | tcgtcataga | 1980 |
| ggaggagatc | atcatgacca | ggtgtgctta | gggaaaatca | tcagcctttg | tcaagttatt | 2040 |

```
gaggactgct gctgccatca gaataaaacc aaccgggcta ctccggaaga ggtcgcggca    2100
aagattgatc agtacctccg tgacgcaaca agtcttgagg aatgcttggc caaacttgag    2160
agagtttccc cgccgagcgc agcggacacc tcctttgatt ggaatgttgt gcttcctggg    2220
gttgaggcga cgaatcagac aaccgaacaa cctcacgtca actcatgctg caccccggtc    2280
cctcccgtga ctcaagagcc tttgggcgag gactcggtcc ctctgaccgc cttctcactg    2340
tccaattgct attaccctgc acaaggtgac gaggttcatc accgtgagag gttaaattcc    2400
gcactctcta agttggaaga ggttgtcctg gaagaatatg ggctcatgtc cactggactt    2460
ggcccgcgac ccgtgctgcc gagcgggctc gacgagctta agaccagat ggaggaggat    2520 ctgctagaac tagccaacac ccaggcgact tcagaaatga tggcctgggc ggctgagcag    2580
gtcgatttaa aagcttgggt caaaagctac ccgcggtgga caccaccacc ccctccacca    2640
agagttcaac ctcgaagaac aaagtctgtc aaaagtttgc cagaggacaa gcctgtccct    2700
gctccgcgca ggaaggtcag atccgattgc ggcagcccgg ttttgatggg cgacaatgtc    2760
cctaacggtt cggaagaaac tgtcggtggt ctcctcaatt ttccgacacc atccgagccg    2820
atgacaccta tgagtgagcc cgtacttgtg cccgcgtcgc gacgtgtccc caagctgatg    2880
acacctttga gtgggtcggc accagttcct gcaccgcgta gaactgtgac aacaacgctg    2940
acgcaccagg atgagcctct ggatttgtct gcgtcctcac aaacggaata tgaggcttcc    3000
cccctaacac catcgcagaa catgggcatc ctggaggcgg ggggggcaaga agctgaggga    3060 gtcctgagtg aaatctcgga tatactaaat gacaccaacc ctgcacctgt gtcatcaagc    3120
agctccctgg gttcagtggc caccgaggat gttccacgca tcctcgggaa aataggagac    3180
actgacgagc tgcttgaccg gggtccctcg gcaccctcca agggagaacc ggtctgtgac    3240
caacctgcca aagatccccg gatgtcgccg cgggagtctg acgagagcat aatagttccg    3300
cccgcagata caggtggtgt cggctcattc actgatttgc cgtcttcaga tggtgtggat    3360
gtggacgggg ggggccgtt aagaacggta aaaacaaaag cagaaaggct cttagatcaa    3420
ctgagctgcc aggttttag cctcgtttcc catctcccta ttttcttctc acacctcttc    3480 aaaatctgaca gtggttattc tccgggtgat tggggttttg cagcttttac tctattttgc    3540
ctctttttat gttacagtta cccattcttc ggttttgctc ccctcttggg tgtattttct    3600
gggtcttctc ggcgtgtgcg aatgggggtt tttggctgct ggttggcttt tgctgttggt    3660
ctgttcaagc ctgtgtccga cccagtcggc actgcttgtg agtttgactc gccagagtgt    3720
aggaacgtcc ttcattcttt tgagcttctc aaaccttggg accctgtccg cagccttgtt    3780 gtgggcccg tcggtctcgg ccttgccatt cttggcaggt tactgggcgg ggcacgctac    3840
atctggcact ttttgcttag gcttggcatt gttgcagact gtgtcttggc tggagcttat    3900
gtgctttctc aaggtaggtg taaaaagtgc tggggatctt gtgtaagaac tgctcctaat    3960
gagatcgcct tcaacgtgtt ccctttacaa cgtgcgacca gtcgtcact catcgacctg    4020 tgcgatcggt tttgcgcacc aaaaggcatg acccccattt ttctcgccac tgggtggcgt    4080
gggtgctgga ccgccggag tcccattgag caaccttctg aaaaacccat cgcgttcgcc    4140
cagctggatg agaagaggat tacggctaga actgtggtcg ctcagcctta tgatcccaac    4200
caggccgtaa agtgcttgcg ggtattacag gcgggtgggg cgatggtggc cgaggcagtc    4260
ccaaaagtgg tcaaagtttc cgctattcca ttccgagctc cttttctttcc cgctggagtg    4320 aaagttgatc ctgagtgcag aatcgtggtt gatcccgata cttttactac agccctccgg    4380
tctggctatt ccaccgcgaa cctcgtcctt ggtacggggg actttgccca gctgaatgga    4440
```

```
ctaaagatca ggcaaatttc caagccttca gggggaggcc cacacctcat tgctgccttg   4500
catgttgcct gctcgatggc gttacacatg cttgctggtg tttatgtaac tgcagtgggg   4560
tcctgcggtg ccggtaccaa cgatccgtgg tgcactaacc cgtttgctgt ccctggctat   4620
ggacctggct ctctttgcac gtctagattg tgcatctccc aacacggcct caccttgccc   4680
ttgacagcac ttgtggcggg attcggcctt caagagattg ccttggtcgt tttgatcttt   4740
gtctccatcg gaggcatggc tcataggttg agttgtaagg ctgacatgtt gtgcatctta   4800
ctcgcaatcg ctagttatgt ttgggtacct cttacctggt tgctttgtgt gtttccttgt   4860
tggttgcgct ggtcctcttt gcaccccctc accatcctgt ggttggtgtt tttcttgatt   4920
tctgtaaata taccctcggg aatcttggcc gtggtgttat tggtttctct ctggctttta   4980
ggtcgttata ctaacattgc tggtctcgtc acccettatg acattcatca ttacaccagt   5040
ggcccccgcg tgtcgccgc cttggccacc gcgccagatg aacctactt ggctgccgtc     5100
cgccgtgctg cgctgactgg tcgtaccatg ctgttcaccc cgtctcagct tgggtccctc   5160
cttgagggcg ctttcagaac tcaaaaaccc tcactgaaca ccgtcaatgt ggtcgggtcc   5220
tccatgggct ctgcggagt gttcactatt gacgggaaaa tcaagtgcgt gactgccgca   5280
catgtcctta cgggtaactc agctagggtt tccggggtcg gcttcaatca aatgcttgac   5340
tttgatgtaa aaggggactt cgccatagct gattgcccga attggcaagg ggttgctccc   5400
aaggcccagt tctgcgagga tgggtggact ggtcgcgcct attggctgac atcctctggc   5460
gttgaacccg tgttattgg gaatgggttc gccttctgct tcaccgcgtg tggcgattct   5520
ggatccccag tgattaccga agccggtgag cttgtcggcg ttcacacagg atcaaacaaa   5580
caaggaggag gcattgtcac gcgcccctca ggccagtttt gtaatgtgaa gcccatcaag   5640
ctgagcgagt tgagtgaatt cttcgctgga cctaaggtcc cgctcggtga tgtgaaaatt   5700
ggcagtcaca taattaatga cacatgcgag gtgccttcag atctttgtgc cctgcttgct   5760
gccaaacccg aactggaagg aggcctttcc acagttcaac ttctgtgtgt gtttttcctc   5820
ctgtggagaa tgatggggca tgcctggacg cccttggttg ctgtggggtt tttcatcctg   5880
aatgagattc tcccagctgt tctggtccgg agtgttttct cctttgggat gttgtgctca   5940
tcttggctca caccatggtc tgcgcaagtc ctgatgatca ggcttctgac agcagccctt   6000
aacagaaaca gatggtctct tggttttttac agccttggtg caataaccag ttttgtcgca   6060
gatcttgcgg taactcaagg gcatccgtta caggtggtaa tgaacttaag cacctatgcc   6120
ttcctgcccc ggatgatggt tgtgacctcg ccagtcccag tgatcgcgtg tggtgttgtg   6180
cacctccttg ccataatttt gtacttgttt aagtaccgct gccttcacaa tgtccttgtt   6240
ggcgatgggg tgttctcttc ggcttttcttc ttgcgatact ttgccgaggg aaagttgagg   6300
gaaggggtgt cgcaatcctg tgggatgagt catgagtcgc tgactggtgc cctcgccatg   6360
agactcactg acgaggactt ggatttcctt acgaaatgga ctgatttaa gtgctttgtt   6420
tctgcgtcca acatgaggaa tgcagcgggc caatttatcg aggctgctta tgcaaaagca   6480
ctaagaattg aacttgctca gttggtacag gttgataagg tccgaggcac catgccaaa    6540
ctcgaggctt tcgccgatac cgtggcaccc caactctcgc ccggtgacat tgttgttgcc   6600
cttggccaca cgcctgttgg cagcatcttc gacctaaagg ttggtagcac caagcatact   6660
ctccaagcta ttgagactag agtccttgcc gggtccaaaa tgactgtggc gcgtgtcgtt   6720
gacccaaccc ccgcaccccc gcccgtacct gtgcccatcc ctctcccacc gaaagttctg   6780
gagaacggtc ccaatgcctg gggggatgag gaccgtttga caagaagaa gaggcgcagg   6840
```

```
atggaagccg tcggcatttt tgtcatggac gggaaaaagt accagaaatt tgggacaag     6900 aattccggtg atgtgtttta tgaggaggtc catattagca cagacgagtg ggagtgcctt     6960
agaactggcg accctgtcga ctttgatcct gagacaggga ttcagtgtgg gcatatcacc     7020
attgaagata aggtttacaa tgtcttcacc tccccatctg gtaggagatt cttggtcccc     7080
gccaaccccg agaatagaag agctcagtgg gaagccgcca agctttccgt ggagcaagcc     7140
cttggtatga tgaacgtcga cggcgaactg actgccaaag aactggagaa actgaaaaga     7200
ataattgaca aactccaggg cctgactaag gagcagtgtt taaactgcta gccgccagcg     7260
gcctgacccg ctgtggtcgc ggcggcttag ttgttactga cagcggta aaaatagtca      7320 aatttcacaa ccggaccttc accccaggac ctgtgaactt aaaagtggcc agtgaggttg     7380
agctaaaaga cgcggttgag cacaaccaac atccggttgc cagaccggtt gatggtggtg     7440
tcgtgctcct gcgctctgca gttccttcgc ttatagatgt cttgatctcc ggcgctgata     7500
catctcctaa gttactcgcc cgccacgggc cgggaaacac tgggattgat ggcacgcttt     7560
gggattttga ggccgaggct actaaagagg aagttgcact cagtgcgcaa ataatacagg     7620
cttgtgatat taggcgcggc gacgcacctg aaattggtct cccttataag ttgtaccctg     7680
ttaggggcaa ccctgagcgg gtaaaaggag ttttacagaa tacaaggttt ggagacatac     7740
cttacaaaac ccccagtgac actggaagcc cggtgcacgc ggctgcctgc ctcacgccta     7800
atgctactcc ggtgactgat gggcgctccg tcttggctac aaccatgccc tctggctttg     7860
agttgtatgt gccgaccatt ccagcgtccg tccttgatta tcttgattct aggcctgact     7920
gccctaaaca gttaacagag cacggttgtg aggatgctgc attaagagac ctctccaagt     7980
atgatttgtc cacccaaggc tttgttttgc ctggagttct tcgccttgtg cggaagtacc     8040
tgttcgccca cgtgggtaag tgcccgcccg ttcatcggcc ttccacttac cctgctaaga     8100
attctatggc tggaataaat gggaacaggt ttccaaccaa ggacattcag agcgtccctg     8160
aaatcgacgt tctgtgcgca caggctgtgc gagaaaactg gcaaactgtt accccttgta     8220
ccctcaagaa acagtactgt gggaagaaga agactaggac aatacttggc accaataact     8280
tcattgcgtt ggcccatcgg gcagcgttga gtggtgttac ccagggcttc atgaaaaaag     8340
cgttcaactc gcccatcgcc ctcgggaaaa acaaatttaa ggagctacaa gccccggtcc     8400
taggcaggtg ccttgaagct gatcttgcgt cctgcgatcg atccacacct gcaattgtcc     8460
gctggtttgc cgccaatctt ctttatgaac tcgcctgtgc tgaggagcat ctaccgtcgt     8520
acgtgctgaa ctgctgccac gacttactgg tcacgcagtc cggcgcggtg actaagagag     8580
gtggcctgtc gtctggcgac ccgattaccc tgtgtcaaa caccatttac agcttagtga     8640
tatatgcaca gcacatggtg ctcagttact tcaaaagtgc tcaccctcat ggccttctgt     8700
ttctgcaaga ccagctgaag tttgaggaca tgctcaaggt tcaaccctg accgtctatt     8760 cggacgacct tgtgctgtat gccgagtctc cctccatgcc aaactaccac tggtgggttg     8820
aacatctgaa ccttatgctg ggtttccaga cggacccaaa gaagacaacc atcacagact     8880
caccatcatt cctaggttgc aggataataa atgggcgcca gctggtccct aaccgtgaca     8940
ggatcctcgc ggccctcgcc taccacatga aggcgagcaa tgtttctgaa tactacgcct     9000
cggcggctgc aatactcatg gacagctgtg cttgtttgga gtatgatcct gaatggtttg     9060
aagagctcgt ggttgggata gcgcagtgcg cccgcaagga cggctacagc tttcctggcc     9120
caccgttctt cttgtccatg tgggaaaaac tcaggtccaa tcatgagggg aagaagtcca     9180
gaatgtgcgg gtactgcggg gccccggctc cgtacgccac tgcctgtggt ctcgatgtct     9240
```

```
gtgtttacca cacccacttc caccagcatt gtcctgttat aatctggtgt ggccacccgg   9300
cgggttctgg ttcttgtagt gagtgcgaac ccccctagg aaaaggcaca agccctctag    9360
atgaggtgtt agaacaagtt ccgtacaagc ctccgcggac tgtgatcatg catgtggagc   9420
agggtctcac ccctcttgac ccaggtagat accagactcg ccgcggattg gtctccgtta   9480
ggcgtggcat caggggaaat gaagtcgacc taccagacgg tgattacgcc agtaccgcct   9540
tgctccctac ttgtaaagag atcaacatgg tcgctgtcgc ctctaacgtg ttgcgcagca   9600
ggtttatcat cggcccaccc ggtgctggga aaacacactg gcttcttcaa caagtccagg   9660
atggtgatgt catttacacg ccaactcacc agaccatgct cgacatgatt agggctttgg   9720
ggacgtgccg gttcaacgtt ccagcaggta aacgctgca attccctgcc cctcccgta    9780 ccggcccatg ggttcgcatc ttggccgcg gttggtgtcc tggcaagaac tccttcctgg   9840
atgaagcggc gtattgcaat caccttgacg tcttgaggct tctcagtaaa acaactctca   9900
cttgcctagg ggacttcaaa caactccacc ctgtgggttt tgactcccat tgctatgtat   9960
ttgacatcat gcctcagacc caattaaaga ccatctggag gttcgggcag aatatctgtg  10020
atgccattca accagattac agggacaaac ttatggccat ggtcaacacg acccgtgtga  10080
cctacgtgga aaacctgtc aggtacgggc aagtcctcac cccctaccac agggaccgag   10140
aggacggcgc cattactatc gactccagtc aaggcgccac atttgatgtg gttacactgc  10200
atttgcccac taaagattca ctcaacaggc aaagagctct tgttgctatc accagggcaa  10260
ggcatgctat cttcgtgtat gacccacaca ggcaattgca gagcatgttt gatcttcccg  10320
cgagaggcac acccgtcaac ctcgcagtgc accgtgacga acagctgatc gtattagaca  10380
gaaacaacag agaaatcacg gttgctcagg ctctaggcaa tggagataaa ttcagggcca  10440
cagataagcg cgttgtagat tctctccgcg ctatttgcgc agacctggaa gggtcgagct  10500
ccccgctccc caaggtcgcg cataacttgg gattccattt ctcacctgat ttgactcagt  10560
ttgctaaact cccggcagaa cttgcacccc actggcccgt ggtgacaacc cagaacaatg  10620
aaaggtggcc agatcggctg gtagccagcc tccgccctat ccataaatat agccgcgcgt  10680
gcattggtgc cggctatatg gtgggcccct cggtgttttt aggcacccct ggggttgtgt  10740
catactatct cacaaaattt gttagaggcg aggctcaagt gcttccggag acagtcttca  10800
gcaccggccg aattgaggta gattgtcgag agtatcttga tgatcgggag cgagaagttg  10860
ctgagtccct cccacatgcc ttcatcggcg atgtcaaagg taccaccgtt ggggatgtc    10920 atcacgttac ctccaaatac cttccgcgct tccttcccaa ggaatcagtt gcggtggtcg  10980
gggtttcgag ccccgggaaa gccgcgaaag cagtttgcac attgacggat gtgtacctcc  11040
cagaccttga agcgtacctc cacccagaga cccagtccag gtgctggaaa gtgatgttgg  11100
actttaagga ggttcgactg atggtatgga agacaagac ggcctatttt caacttgaag   11160
gccgccattt tacctggtat caacttgcaa gctacgcctc atacatccga gttcctgtta  11220
attctactgt gtacttggac ccctgcatgg gccctgctct ttgcaacagg agggttgtcg  11280
ggtccaccca ttggggagct gacctcgcag tcacccctta tgattacggt gccaaaatta  11340
ttctgtctag tgcataccat ggtgaaatgc ctccaggtta caaaattctg gcgtgcgcgg  11400
agttctcgct tgatgatcca gtaaggtaca aacacacctg gggatttgaa tcggatacag  11460
cgtatctgta cgagtttact ggaaatggtg aggactggga ggattacaat gatgcgtttc  11520
gggcgcgcca gaaagggaaa attttataaag ctaatgccac cagcatgagg tttcattttc  11580
ccccgggccc tgtcattgaa ccaactttag gcctgaattg aaatgaaatg gggtctatgc  11640
```

```
aaagcctctt tgacaaaatt ggccaacttt ttgtggatgc tttcacggaa tttctggtgt   11700
ccattgttga tatcatcata tttttggcca ttttgtttgg cttcacaatc gccggttggc   11760
tggtggtctt atgcatcaga ctggtttgct ccgcggtact ccgtgcgcgc tctaccgttc   11820
accctgagca attacagaag atcttatgag gcctttcttt ctcagtgtca ggtagacatt   11880
cccacctggg gcgtcaaaca ccctttgggg gtgctttggc accataaggt gtcaaccctg   11940
attgatgaaa tggtgtcgcg tcgaatgtac cgcgtcatgg aaaaagcagg gcaggctgcc   12000
tggaaacagg tggtgagcga ggctacattg tctcgcatta gtggtttgga tgtggtggct   12060
cattttcaac atcttgccgc tattgaagcc gagacttgta aatatttggc ttcccggcta   12120
cccatgctgc acaacctgcg cttgacaggg tcaaatgtaa ccatagtgta taatagtact   12180
ttggatcagg tgtttgccat tttcccaacc cctggttccc ggccaaagct tcatgatttt   12240
cagcaatggc taatagctgt acattcctcc atatttcct ccgttgcagc ttcttgtact   12300 cttttgttg tgctgtggtt gcgaattcca atgctacgtt ctgttttgg tttccgctgg   12360 ttaggggcaa cttttctttt gaactcatgg tgaattacac ggtatgcccg ctttgcccaa   12420
cccggcaggg agccgccgag atccttgaac ccggcaagtc ttttggtgc aggatagggc   12480 atgaccgatg tagtgagaac gatcatgacg aactagggtt catggttccg cctggcctct   12540
ccagcgaagg ccacttgacc agtgtttacg cctggttggc gttcctgtcc ttcagctaca   12600
cggcccagtt ccatcccgag atatttggga tagggaatgt gagtcaagtt tatgttgaca   12660
tcaagcacca actcatctgc gctgttcatg acggggataa cgccaccttg cctcgccatg   12720
acaatatttc agccgtattt cagacctact accaacacca ggtcgacggc ggcaattggt   12780
ttcacctgga atggctacgc ccttttcttt cctcttggtt ggttttaaat gtttcgtggt   12840
ttctcaggcg ttcgcctgca agccatgttt cagttcgagt ctttcggaca tcaaaaccaa   12900
caccaccgca gcatcaggct tcgttgtcct ccaggacatc agctgcctta ggcatggcga   12960
ctcgtcctct ccgacgattc gcaaaagttc tcagtgccgc acggcgatag ggacgcccgt   13020
gtacatcacc atcactgcca atgtcacaga tgaaaattat ctacattctt ctgatctcct   13080
catgctttct tcttgccttt tctatgcttc cgagatgagt gaaaagggat tcaaagtggt   13140
gtttggcaat gtgtcaggca tcgtggctgt gtgcgtcaac tttaccagct acgtccaaca   13200
cgtcaaggag tttacccaac gctccttagt ggtcgatcat gtgcgactgc ttcatttcat   13260
gacacctgag accatgaggt gggcaaccgt tttagcctgt ctttttgcca tccctactgg   13320
caatttgaat gttcaagtat gttggggaag tgcttaccg cgtgctgttg ctcgcgattg   13380
ctttttttgt ggtgtatcgt gccgtcctat cttgctgtgc tcgtcaacgc cagcaacaac   13440
aacagctctc atattcagtt gatttataac ttaacgctat gtgagctgaa tggcacagat   13500
tggctggcac aaaaatttga ctgggcagtg gagacttttg tcatcttccc cgtgttgact   13560
cacattgttt cctatgtggc actcaccacc agccatttcc ttgacacagt tggtctggcc   13620
actgtgtcca ccgccggata ttatcacggg cggtatgtct tgagtagcat ttacgcagtc   13680
tgtgctctgg ctgcgctgat ttgctttgtc attaggcttg cgaagaactg catgtcctgg   13740
cgctactctt gtaccagata taccaacttc cttctggaca ctaagggcaa actctatcgt   13800
tggcggtcgc ccgtcattgt ggagaaaggg ggtaaggttg aggtcgaagg tcacctgatc   13860
gacctcaaga gagttgtgct tgatggttcc gcggcaaccc ctttaaccag agtttcagcg   13920
gaacgatggg gtcgtctcta gacgacttct gcaatgatag cacagctcca cagaaggtgc   13980
ttttggcgtt ttccattacc tacacgccag tgatgatata tgctctaaag gtaagtcgcg   14040
```

```
gccgactgct agggcttctg cacctttga tctttctgaa ttgtgctttt accttcgggt    14100
acatgacatt cgtgcacttt gagagcacaa atagggtcgc gctcactatg ggagcagtag    14160
ttgcacttct ttggggagtg tactcagcca tagaaacctg gaaattcatc acctccagat    14220
gccgtttgtg cttgctaggc cgcaagtaca ttctggcccc tgcccaccac gtcgaaagtg    14280
ccgcgggctt tcatccgatt gcggcaaatg ataaccacgc atttgtcgtc cggcgtcccg    14340
gctccactac ggtcaacggc acattggtgc ccggggttgaa aagcctcgtg ttgggtggca    14400
gaaaagctgt taagcaggga gtggtaaacc ttgttaaata tgccaaataa caacggcaag    14460
cagcaaaaga aaagaaggg gaatggccag ccagtcaatc agctgtgcca atgctgggt    14520
aagatcatcg cccaacaaaa ccagtccaga ggcaagggac cggggaagaa aaataggaag    14580
aaaaacccgg ggaagcccca tttccctcta gcgactgaag atgacgtcag gcatcacttt    14640
acccctagtg agcggcaatt gtgtctgtcg tcgatccaga ctgccttcaa tcagggtgct    14700
ggaacttgtg ccctgtcaga ttcagggagg ataagttaca ctgtggagtt tagtttgccg    14760
acgcaacata ctgtgcgtct gatccgcgcc acagcatcac cctcagcatg atgggctggc    14820
attctttggc acctcagtgt tagaattggg agaatgtgtg gtgaatgcca ctgattgaca    14880
ctgtgcctct aagtcaccta ttcaattagg gcgaccgtgt gggggtaaag tttaattggc    14940
gagaaccatg cggccgtaat taaaaa                                         14966
```

<210> SEQ ID NO 2
<211> LENGTH: 950
<212> TYPE: PRT
<213> ORGANISM: Porcine reproductive and respiratory syndrome virus

<400> SEQUENCE: 2

```
Ala Gly Lys Arg Ala Arg Lys Pro Arg Ser Gly Ala Thr Thr Met Val
 1               5                  10                  15

Ala His His Ala Ser Ser Ala His Glu Thr Arg Gln Ala Thr Lys His
            20                  25                  30

Glu Gly Ala Gly Ala Asn Lys Ala Glu His Leu Lys Arg Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Asn Phe Glu Thr Thr Leu Pro Glu Arg Val Arg
65                  70                  75                  80

Pro Ser Asp Asp Trp Ala Thr Asp Glu Asp Leu Val Asn Thr Ile Gln
                85                  90                  95

Ile Leu Arg Leu Pro Ala Ala Leu Asp Arg Asn Gly Ala Cys Gly Ser
            100                 105                 110

Ala Lys Tyr Val Leu Lys Leu Glu Gly Glu His Trp Thr Val Ser Val
        115                 120                 125

Ile Pro Gly Met Ser Pro Thr Leu Leu Pro Leu Glu Cys Val Gln Gly
    130                 135                 140

Cys Cys Glu His Lys Gly Gly Leu Val Ser Pro Asp Ala Val Glu Ile
145                 150                 155                 160

Ser Gly Phe Asp Pro Ala Cys Leu Asp Arg Leu Ala Lys Val Met His
                165                 170                 175

Leu Pro Ser Ser Thr Ile Pro Ala Ala Leu Ala Glu Leu Ser Asp Asp
            180                 185                 190

Ser Asn Arg Pro Val Ser Pro Ala Ala Thr Thr Trp Thr Val Ser Gln
        195                 200                 205

Phe Tyr Ala Arg His Arg Gly Gly Asp His His Asp Gln Val Cys Leu
```

```
            210                 215                 220
Gly Lys Ile Ile Ser Leu Cys Gln Val Ile Glu Asp Cys Cys His
225                 230                 235                 240

Gln Asn Lys Thr Asn Arg Ala Thr Pro Glu Glu Val Ala Ala Lys Ile
                245                 250                 255

Asp Gln Tyr Leu Arg Gly Ala Thr Ser Leu Glu Glu Cys Leu Ala Lys
                260                 265                 270

Leu Glu Arg Val Ser Pro Ser Ala Ala Asp Thr Ser Phe Asp Trp
            275                 280                 285

Asn Val Val Leu Pro Gly Val Glu Ala Ala Asn Gln Thr Thr Glu Gln
290                 295                 300

Pro His Val Asn Ser Cys Cys Thr Leu Val Pro Pro Val Thr Gln Glu
305                 310                 315                 320

Pro Leu Gly Lys Asp Ser Val Pro Leu Thr Ala Phe Ser Leu Ser Asn
                325                 330                 335

Cys Tyr Tyr Pro Ala Gln Gly Asp Glu Val His His Arg Glu Arg Leu
            340                 345                 350

Asn Ser Val Leu Ser Lys Leu Glu Glu Val Val Leu Glu Glu Tyr Gly
                355                 360                 365

Leu Met Ser Thr Gly Leu Gly Pro Arg Pro Val Leu Pro Ser Gly Leu
370                 375                 380

Asp Glu Leu Lys Asp Gln Met Glu Glu Asp Leu Leu Lys Leu Ala Asn
385                 390                 395                 400

Thr Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro
            420                 425                 430

Pro Pro Arg Val Gln Pro Arg Arg Thr Lys Ser Val Lys Ser Leu Pro
            435                 440                 445

Glu Gly Lys Pro Val Pro Ala Pro Arg Arg Lys Val Arg Ser Asp Cys
            450                 455                 460

Gly Ser Pro Val Leu Met Gly Asp Asn Val Pro Asn Gly Ser Glu Glu
465                 470                 475                 480

Thr Val Gly Gly Pro Leu Asn Leu Pro Thr Pro Ser Glu Pro Met Thr
                485                 490                 495

Pro Met Ser Glu Pro Val Leu Val Pro Ala Ser Arg Arg Val Pro Lys
            500                 505                 510

Leu Met Thr Pro Leu Ser Gly Ser Ala Pro Val Pro Ala Pro Arg Arg
            515                 520                 525

Thr Val Thr Thr Thr Leu Thr His Gln Asp Glu Pro Leu Asp Leu Ser
            530                 535                 540

Ala Ser Ser Gln Thr Glu Tyr Glu Ala Phe Pro Leu Ala Pro Ser Gln
545                 550                 555                 560

Asn Met Gly Ile Leu Glu Ala Gly Gly Gln Val Glu Glu Val Leu
                565                 570                 575

Ser Glu Ile Ser Asp Ile Leu Asn Asp Thr Asn Pro Ala Pro Val Ser
            580                 585                 590

Ser Ser Ser Ser Leu Ser Ser Val Lys Ile Thr Arg Pro Lys Tyr Ser
            595                 600                 605

Ala Gln Ala Ile Ile Asp Ser Gly Gly Pro Cys Ser Gly His Leu Gln
            610                 615                 620

Lys Glu Lys Glu Ala Cys Leu Ser Ile Met Arg Glu Ala Cys Asp Ala
625                 630                 635                 640
```

```
Ser Lys Leu Gly Asp Pro Ala Thr Gln Glu Trp Leu Ser Arg Met Trp
            645                 650                 655

Asp Arg Val Asp Met Leu Thr Trp Arg Asn Thr Ser Ala Tyr Gln Ala
        660                 665                 670

Phe Arg Ile Leu Asn Gly Arg Phe Glu Phe Leu Pro Lys Met Ile Leu
        675                 680                 685

Glu Thr Pro Pro His Pro Cys Gly Phe Val Met Leu Pro Arg Thr
        690                 695                 700

Pro Ala Pro Ser Val Ser Ala Glu Ser Asp Leu Thr Ile Gly Ser Val
705                 710                 715                 720

Ala Thr Glu Asp Val Pro Arg Ile Leu Gly Lys Ile Gly Asp Thr Asp
            725                 730                 735

Glu Leu Leu Asp Arg Gly Pro Ser Ala Pro Ser Lys Gly Glu Pro Val
        740                 745                 750

Cys Asp Gln Pro Ala Lys Asp Pro Arg Met Ser Pro Arg Glu Ser Asp
        755                 760                 765

Glu Ser Met Ile Ala Pro Pro Ala Asp Thr Gly Gly Val Gly Ser Phe
770                 775                 780

Thr Asp Leu Pro Ser Ser Asp Gly Val Asp Val Asp Gly Gly Pro
785                 790                 795                 800

Leu Arg Thr Val Lys Thr Lys Ala Gly Arg Leu Leu Asp Gln Leu Ser
            805                 810                 815

Cys Gln Val Phe Ser Leu Val Ser His Leu Pro Ile Phe Phe Ser His
        820                 825                 830

Leu Phe Lys Ser Asp Ser Gly Tyr Ser Pro Gly Asp Trp Gly Phe Ala
        835                 840                 845

Ala Phe Thr Leu Phe Cys Leu Phe Leu Cys Tyr Ser Tyr Pro Phe Phe
850                 855                 860

Gly Phe Ala Pro Leu Leu Gly Val Phe Ser Gly Ser Ser Arg Arg Val
865                 870                 875                 880

Arg Met Gly Val Phe Gly Cys Trp Leu Ala Phe Ala Val Gly Leu Phe
            885                 890                 895

Lys Pro Val Ser Asp Pro Val Gly Thr Ala Cys Glu Phe Asp Ser Pro
        900                 905                 910

Glu Cys Arg Asn Val Leu His Ser Phe Glu Leu Leu Lys Pro Trp Asp
        915                 920                 925

Pro Val Arg Ser Leu Val Val Gly Pro Val Gly Leu Gly Leu Ala Ile
930                 935                 940

Leu Gly Arg Leu Leu Gly
945                 950

<210> SEQ ID NO 3
<211> LENGTH: 2850
<212> TYPE: DNA
<213> ORGANISM: Porcine reproductive and respiratory syndrome virus

<400> SEQUENCE: 3
gccggaaaga gagcaaggaa accgcgctct ggtgcgacta ctatggtcgc tcatcacgct      60
tcgtccgctc atgaaacccg gcaggccacg aagcacgagg gtgccggcgc taacaaggct     120
gagcatctca gcgctactc tccgcctgcc gaagggaact gtggttggca ctgcatttcc     180
gccatcgcca accggatggt gaattccaac tttgagacca cccttcctga agagtaagg     240 ccttcagatg actgggccac tgacgaggat cttgtgaaca ccatccaaat cctcaggctc     300
cctgcggcct tggacaggaa cggcgcttgc ggtagcgcca agtacgtgct taaactggag     360
```

```
ggtgagcatt ggactgtctc tgtgatccct gggatgtccc ctactttgct ccccottgaa      420 tgtgttcagg gttgttgtga gcataagggc ggtcttgttt ccccggatgc ggtcgaaatt      480
tccggatttg atcctgcctg ccttgaccga ctggctaagg taatgcactt gcctagcagt      540
accatcccag ccgctctggc cgaattgtcc gacgactcca accgtccggt ttccccggcc      600
gctactacgt ggactgtttc gcaattctat gctcgtcata gaggaggaga tcatcatgac      660
caggtgtgct tagggaaaat catcagcctt tgtcaagtta ttgaggattg ctgctgccat      720
cagaataaaa ccaaccgggc tactccggaa gaggtcgcgg caaagattga tcagtacctc      780
cgtggcgcaa caagtcttga ggaatgcttg gccaaacttg agagagtttc cccgccgagc      840
gctgcggaca cctcctttga ttggaatgtt gtgcttcctg gggttgaggc ggcgaatcag      900
acaaccgaac aacctcacgt caactcatgc tgcaccctag tccctcccgt gactcaagag      960
cctttgggca aggactcggt ccctctgacc gccttctcac tgtccaattg ctattaccct     1020
gcacaaggtg acgaggttca tcaccgtgag aggttaaatt ccgtactctc taagttggaa     1080
gaggttgtcc tggaagaata tgggctcatg tccactggac ttggcccgcg acccgtgctg     1140
ccgagcgggc tcgacgagct taaagaccag atggaggagg atctgctaaa actagccaac     1200
acccaggcga cttcagaaat gatggcctgg gcggctgagc aggtcgattt aaaagcttgg     1260
gtcaaaagct acccgcggtg gacaccacca ccccaccac caagagttca acctcgaaga     1320
acaaagtctg tcaaaagctt gccagagggc aagcctgtcc ctgctccgcg caggaaggtc     1380
agatccgatt gcggcagccc ggttttgatg ggcgacaatg tccctaacgg ttcggaagaa     1440
actgtcggtg gtcccctcaa tcttccgaca ccatccgagc cgatgacacc tatgagtgag     1500
cccgtacttg tgccagcgtc gcgacgtgtc cccaagctga tgacaccttt gagtgggtcg     1560
gcaccagttc ctgcaccgcg tagaactgta acaacaacgc tgacgcacca ggatgagcct     1620
ctggatttgt ctgcgtcctc acagacgaaa tatgaggctt ccccctagc accatcgcag      1680 aacatgggta tcctggaggc gggggggcaa gaagttgagg aagtcctgag tgaaatctcg     1740
gatatactaa atgacaccaa ccctgcacct gtgtcatcaa gcagctccct gtcaagtgtt     1800
aagatcacac gcccaaaata ctcagctcaa gccatcatcg actctggcgg gccttgcagt     1860
gggcatctcc aaaaggaaaa agaagcatgc ctcagcatca tgcgtgaggc ttgtgatgcg     1920
tccaagcttg gtgatcctgc tacgcaggag tggctctctc gcatgtggga tagggttgac     1980
atgctgactt ggcgcaacac gtctgcttac caggcgtttc gcatcttaaa tggcaggttt     2040
gagtttctcc caaagatgat tctcgagaca ccgccgcccc accgtgcgg gtttgtgatg     2100 ttacctcgca cgcctgcacc ttccgtgagt gcagagagtg acctcaccat tggttcagtg     2160
gccaccgagt atgttccacg catcctcggg aaaataggag acaccgacga gctgcttgac     2220
cggggtccct cggcacccte caagggagaa ccggtctgtg accaacctgc caaagatccc     2280
cggatgtcgc cgcgggagtc tgacgagagc atgatagctc cgcccgcaga tacaggtggt     2340
gtcggctcat tcactgattt gccgtcttca gatggtgtgg atgtggacgg ggggggccg      2400 ttaagaacgg taaaaacaaa agcaggaagg ctcttagacc aactgagctg ccaggttttt     2460
agcctcgttt cccatctccc tatttttctt cacacctct tcaaatctga cagtggttat      2520
tctccgggtg attggggttt tgcagctttt actctatttt gcctctttct atgttacagt     2580
tacccattct tcggttttgc tcccctcttg ggtgtatttt ctgggtcttc tcggcgtgtg     2640
cgaatggggt tttttggctg ctggttggct tttgctgttg gtctgttcaa gcctgtgtcc     2700
gacccagtcg gcactgcttg tgagtttgac tcgccagagt gtaggaacgt ccttcattct     2760
```

```
tttgagcttc tcaaaccttg ggaccctgtc cgcagccttg ttgtgggccc cgtcggtctc    2820
ggccttgcca ttcttggcag gttactgggc                                    2850
```

<210> SEQ ID NO 4
<211> LENGTH: 830
<212> TYPE: PRT
<213> ORGANISM: Porcine reproductive and respiratory syndrome virus

<400> SEQUENCE: 4

```
Ala Gly Lys Arg Ala Arg Lys Thr Arg Ser Gly Ala Thr Thr Met Val
 1               5                  10                  15

Ala His His Ala Ser Ser Ala His Lys Ile Arg Gln Ala Thr Lys His
            20                  25                  30

Glu Gly Ala Gly Ala Asn Lys Ala Glu His Leu Lys Arg Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Asn Phe Glu Thr Thr Leu Pro Glu Arg Val Arg
65                  70                  75                  80

Pro Ser Asp Asp Trp Ala Thr Asp Glu Asp Leu Val Asn Thr Ile Gln
                85                  90                  95

Ile Leu Arg Leu Pro Ala Ala Leu Asp Arg Asn Gly Ala Cys Gly Ser
            100                 105                 110

Ala Lys Tyr Val Leu Lys Leu Glu Gly Glu His Trp Thr Val Ser Val
        115                 120                 125

Ile Pro Gly Met Ser Pro Thr Leu Leu Pro Leu Glu Cys Val Gln Gly
    130                 135                 140

Cys Cys Glu His Lys Gly Gly Leu Val Ser Pro Asp Ala Val Glu Ile
145                 150                 155                 160

Ser Gly Phe Asp Pro Ala Cys Leu Asp Arg Leu Ala Lys Val Met His
                165                 170                 175

Leu Pro Ser Ser Thr Ile Pro Ala Ala Leu Ala Glu Leu Ser Asp Asp
            180                 185                 190

Ser Asn Arg Pro Val Ser Pro Ala Ala Thr Thr Trp Thr Val Ser Gln
        195                 200                 205

Phe Tyr Ala Arg His Arg Gly Gly Asp His His Asp Gln Val Cys Leu
    210                 215                 220

Gly Lys Ile Ile Ser Leu Cys Gln Val Ile Glu Asp Cys Cys Cys His
225                 230                 235                 240

Gln Asn Lys Thr Asn Arg Ala Thr Pro Glu Glu Val Ala Ala Lys Ile
                245                 250                 255

Asp Gln Tyr Leu Arg Asp Ala Thr Ser Leu Glu Glu Cys Leu Ala Lys
            260                 265                 270

Leu Glu Arg Val Ser Pro Pro Ser Ala Ala Asp Thr Ser Phe Asp Trp
        275                 280                 285

Asn Val Val Leu Pro Gly Val Glu Ala Thr Asn Gln Thr Thr Glu Gln
    290                 295                 300

Pro His Val Asn Ser Cys Cys Thr Pro Val Pro Pro Val Thr Gln Glu
305                 310                 315                 320

Pro Leu Gly Glu Asp Ser Val Pro Leu Thr Ala Phe Ser Leu Ser Asn
                325                 330                 335

Cys Tyr Tyr Pro Ala Gln Gly Asp Glu Val His His Arg Glu Arg Leu
            340                 345                 350

Asn Ser Ala Leu Ser Lys Leu Glu Glu Val Val Leu Glu Glu Tyr Gly
        355                 360                 365
```

```
Leu Met Ser Thr Gly Leu Gly Pro Arg Pro Val Leu Pro Ser Gly Leu
    370                 375                 380

Asp Glu Leu Lys Asp Gln Met Glu Glu Asp Leu Leu Glu Leu Ala Asn
385                 390                 395                 400

Thr Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro Pro
                420                 425                 430

Pro Pro Arg Val Gln Pro Arg Arg Thr Lys Ser Val Lys Ser Leu Pro
            435                 440                 445

Glu Asp Lys Pro Val Pro Ala Pro Arg Arg Lys Val Arg Ser Asp Cys
        450                 455                 460

Gly Ser Pro Val Leu Met Gly Asp Asn Val Pro Asn Gly Ser Glu Glu
465                 470                 475                 480

Thr Val Gly Gly Leu Leu Asn Phe Pro Thr Pro Ser Glu Pro Met Thr
                485                 490                 495

Pro Met Ser Glu Pro Val Leu Val Pro Ala Ser Arg Arg Val Pro Lys
            500                 505                 510

Leu Met Thr Pro Leu Ser Gly Ser Ala Pro Val Pro Ala Pro Arg Arg
            515                 520                 525

Thr Val Thr Thr Thr Leu Thr His Gln Asp Glu Pro Leu Asp Leu Ser
    530                 535                 540

Ala Ser Ser Gln Thr Glu Tyr Glu Ala Ser Pro Leu Thr Pro Ser Gln
545                 550                 555                 560

Asn Met Gly Ile Leu Glu Ala Gly Gly Gln Glu Ala Glu Gly Val Leu
                565                 570                 575

Ser Glu Ile Ser Asp Ile Leu Asn Asp Thr Asn Pro Ala Pro Val Ser
            580                 585                 590

Ser Ser Ser Ser Leu Gly Ser Val Ala Thr Glu Asp Val Pro Arg Ile
        595                 600                 605

Leu Gly Lys Ile Gly Asp Thr Asp Glu Leu Leu Asp Arg Gly Pro Ser
610                 615                 620

Ala Pro Ser Lys Gly Glu Pro Val Cys Asp Gln Pro Ala Lys Asp Pro
625                 630                 635                 640

Arg Met Ser Pro Arg Glu Ser Asp Glu Ser Ile Ile Val Pro Pro Ala
                645                 650                 655

Asp Thr Gly Gly Val Gly Ser Phe Thr Asp Leu Pro Ser Ser Asp Gly
            660                 665                 670

Val Asp Val Asp Gly Gly Gly Pro Leu Arg Thr Val Lys Thr Lys Ala
        675                 680                 685

Glu Arg Leu Leu Asp Gln Leu Ser Cys Gln Val Phe Ser Leu Val Ser
    690                 695                 700

His Leu Pro Ile Phe Phe Ser His Leu Phe Lys Ser Asp Ser Gly Tyr
705                 710                 715                 720

Ser Pro Gly Asp Trp Gly Phe Ala Ala Phe Thr Leu Phe Cys Leu Phe
                725                 730                 735

Leu Cys Tyr Ser Tyr Pro Phe Phe Gly Phe Ala Pro Leu Leu Gly Val
            740                 745                 750

Phe Ser Gly Ser Ser Arg Arg Val Arg Met Gly Val Phe Gly Cys Trp
        755                 760                 765

Leu Ala Phe Ala Val Gly Leu Phe Lys Pro Val Ser Asp Pro Val Gly
    770                 775                 780

Thr Ala Cys Glu Phe Asp Ser Pro Glu Cys Arg Asn Val Leu His Ser
```

| | | | |
|---|---|---|---|
| 785 | 790 | 795 | 800 |

Phe Glu Leu Leu Lys Pro Trp Asp Pro Val Arg Ser Leu Val Val Gly
                       805                  810                  815

Pro Val Gly Leu Gly Leu Ala Ile Leu Gly Arg Leu Leu Gly
               820                  825                  830

<210> SEQ ID NO 5
<211> LENGTH: 2490
<212> TYPE: DNA
<213> ORGANISM: Porcine reproductive and respiratory syndrome virus

<400> SEQUENCE: 5

| | | |
|---|---|---|
| gccggaaaga gagcaaggaa acacgctct ggtgcgacta ctatggtcgc tcatcacgct | 60 |
| tcgtccgctc ataaaatccg gcaggccacg aagcacgagg gtgccggcgc taacaaggct | 120 |
| gagcatctca agcgctactc tccgcctgcc gaagggaact gtggttggca ctgcatttcc | 180 |
| gccatcgcca accggatggt gaattccaac tttgagacca cccttcctga aagagtaagg | 240 |
| ccttcagatg actgggccac tgacgaggat cttgtgaata ccatccaaat cctcaggctc | 300 |
| cctgcggcct tggacaggaa cggcgcttgc ggtagcgcca agtacgtgct taaactggag | 360 |
| ggtgagcatt ggactgtctc tgtgatccct gggatgtccc ctactttgct cccccttgaa | 420 |
| tgtgttcagg gttgttgtga acataagggc ggtcttgttt cccggatgc ggtcgaaatt | 480 |
| tccggatttg atcctgcctg ccttgaccga ctggctaagg taatgcactt gcctagcagt | 540 |
| accatcccag ccgctctggc cgaattgtcc gacgactcca accgtccggt ttccccggcc | 600 |
| gctactacgt ggactgtttc gcaattctat gctcgtcata gaggaggaga tcatcatgac | 660 |
| caggtgtgct tagggaaaat catcagcctt tgtcaagtta ttgaggactg ctgctgccat | 720 |
| cagaataaaa ccaaccgggc tactccggaa gaggtcgcgg caaagattga tcagtacctc | 780 |
| cgtgacgcaa caagtcttga ggaatgcttg gccaaacttg agagagtttc cccgccgagc | 840 |
| gcagcggaca cctcctttga ttggaatgtt gtgcttcctg gggttgaggc gacgaatcag | 900 |
| acaaccgaac aacctcacgt caactcatgc tgcacccgg tccctcccgt gactcaagag | 960 |
| cctttgggcg aggactcggt ccctctgacc gccttctcac tgtccaattg ctattaccct | 1020 |
| gcacaaggtg acgaggttca tcaccgtgag aggttaaatt ccgcactctc taagttggaa | 1080 |
| gaggttgtcc tggaagaata tgggctcatg tccactggac ttggccccgcg acccgtgctg | 1140 |
| ccgagcgggc tcgacgagct taaagaccag atggaggagg atctgctaga actagccaac | 1200 |
| acccaggcga cttcagaaat gatggcctgg gcggctgagc aggtcgattt aaaagcttgg | 1260 |
| gtcaaaagct acccgcggtg gacaccacca ccccctccac caagagttca acctcgaaga | 1320 |
| acaaagtctg tcaaaagttt gccagaggac aagcctgtcc ctgctccgcg caggaaggtc | 1380 |
| agatccgatt gcggcagccc ggttttgatg ggcgacaatg tccctaacgg ttcggaagaa | 1440 |
| actgtcggtg gtctcctcaa ttttccgaca ccatccgagc cgatgacacc tatgagtgag | 1500 |
| cccgtacttg tgcccgcgtc gcgacgtgtc cccaagctga tgacccttt gagtgggtcg | 1560 |
| gcaccagttc ctgcaccgcg tagaactgtg acaacaacgc tgacgcacca ggatgagcct | 1620 |
| ctggatttgt ctgcgtcctc acaaacggaa tatgaggctt ccccccctaac accatcgcag | 1680 |
| aacatgggca tcctggaggc ggggggccaa gaagctgagg gagtcctgag tgaaatctcg | 1740 |
| gatatactaa atgacaccaa ccctgcacct gtgtcatcaa gcagctccct gggttcagtg | 1800 |
| gccaccgagg atgttccacg catcctcggg aaaataggag acactgacga gctgcttgac | 1860 |
| cggggtccct cggcacccct caagggagaa ccggtctgtg accaacctgc caagatccc | 1920 |

```
                                                                      -continued cggatgtcgc cgcgggagtc tgacgagagc ataatagttc cgcccgcaga tacaggtggt      1980
gtcggctcat tcactgattt gccgtcttca gatggtgtgg atgtggacgg ggggggggccg     2040 ttaagaacgg taaaaacaaa agcagaaagg ctcttagatc aactgagctg ccaggttttt     2100
agcctcgttt cccatctccc tatttcttc tcacacctct tcaaatctga cagtggttat     2160
tctccgggtg attggggttt tgcagctttt actctatttt gcctcttttt atgttacagt     2220
tacccattct tcggttttgc tcccctcttg ggtgtatttt ctgggtcttc tcggcgtgtg     2280
cgaatggggg ttttggctg ctggttggct tttgctgttg gtctgttcaa gcctgtgtcc     2340
gacccagtcg gcactgcttg tgagtttgac tcgccagagt gtaggaacgt ccttcattct     2400
tttgagcttc tcaaaccttg ggaccctgtc cgcagccttg ttgtgggccc cgtcggtctc     2460
ggccttgcca ttcttggcag gttactgggc                                     2490

<210> SEQ ID NO 6
<211> LENGTH: 120
<212> TYPE: PRT
<213> ORGANISM: Porcine reproductive and respiratory syndrome virus

<400> SEQUENCE: 6

Ser Ser Val Lys Ile Thr Arg Pro Lys Tyr Ser Ala Gln Ala Ile Ile
1               5                   10                  15

Asp Ser Gly Gly Pro Cys Ser Gly His Leu Gln Lys Glu Lys Glu Ala
            20                  25                  30

Cys Leu Ser Ile Met Arg Glu Ala Cys Asp Ala Ser Lys Leu Gly Asp
        35                  40                  45

Pro Ala Thr Gln Glu Trp Leu Ser Arg Met Trp Asp Arg Val Asp Met
    50                  55                  60

Leu Thr Trp Arg Asn Thr Ser Ala Tyr Gln Ala Phe Arg Ile Leu Asn
65                  70                  75                  80

Gly Arg Phe Glu Phe Leu Pro Lys Met Ile Leu Glu Thr Pro Pro Pro
                85                  90                  95

His Pro Cys Gly Phe Val Met Leu Pro Arg Thr Pro Ala Pro Ser Val
            100                 105                 110

Ser Ala Glu Ser Asp Leu Thr Ile
        115                 120

<210> SEQ ID NO 7
<211> LENGTH: 360
<212> TYPE: DNA
<213> ORGANISM: Porcine reproductive and respiratory syndrome virus

<400> SEQUENCE: 7
tcaagtgtta agatcacacg cccaaaatac tcagctcaag ccatcatcga ctctggcggg      60
ccttgcagtg ggcatctcca aaaggaaaaa gaagcatgcc tcagcatcat gcgtgaggct     120
tgtgatgcgt ccaagcttgg tgatcctgct acgcaggagt ggctctctcg catgtgggat     180
agggttgaca tgctgacttg cgcaacacg tctgcttacc aggcgtttcg catcttaaat     240
ggcaggtttg agtttctccc aaagatgatt ctcgagacac cgccgcccca cccgtgcggg     300
tttgtgatgt tacctcgcac gcctgcacct tccgtgagtg cagagagtga cctcaccatt     360
```

ATTENUATED LIVE VACCINE FOR PREVENTION OF PORCINE REPRODUCTIVE AND RESPIRATORY SYNDROME

TECHNICAL FIELD

The present disclosure relates to an attenuated live vaccine for preventing pigs from infection of porcine reproductive and respiratory syndrome virus.

BACKGROUND OF THE INVENTION

Porcine Reproductive and Respiratory Syndrome (PRRS) is a swine infectious disease caused by PRRSV (Porcine Reproductive and Respiratory Syndrome Virus). The clinical manifestations of the disease include reproductive disorders in sows and respiratory distress in piglets. Early stage symptoms include fever, lethargy, anorexia, listlessness, respiratory distress, cough and etc. The disease was first identified in North Carolina of the United States (in 1987), and it was subsequently found in Canada (in 1998), Germany (in 1990) and Britain (in 1991). The disease was named as Porcine Reproductive and Respiratory Syndrome (PRRS) by The World Organization for Animal Health (OIE) in 1992. The epidemic of PRRS was reported in China in 1996. PRRSV can be divided into two genotypes: American type and European type. The antigen typing is generally consistent with the respective genotype. The two genotypes have relatively significant differences in antigen types.

The PRRS epidemic caused enormous economic loss to world pork industry. Therefore, prevention of PRRS has received an increasing attention from practitioners worldwide. Vaccine preventions have made certain progress. Inactivated vaccines, which are made during the early development stage, do not involve risks in virus shedding or return of virulence. However, inactivated vaccines cannot provide ideal protection against PRRSV which is primarily eliminated through cell-mediated immunity.

In 1995, Boehringer Ingleheim in the United States provided for the first time an attenuated live vaccine called Resp PRRS/Repro™, which was approved for immunization in 3-18 week old healthy young sows, multiparous sows, suckling piglets, and wean-to-finish pigs for an immunization period of above 4 months. Another attenuated vaccine Prime Pac® PRRS, manufactured by Schering-Plough Animal Health, is used for preventative inoculation in sows or gilts at 3-6 weeks before breeding, and it has shown good preventative effects. However, as PRRSV is prone to mutate, the attenuated vaccines cannot provide desirable preventative clinical effects, which can be the main reason for reoccurrence of PRRS in pig farms.

In 2006, China was hit by an outbreak of highly pathogenic porcine reproductive and respiratory syndrome, and the causative pathogen of this epidemic was a mutated PRRSV strain, which contained a significant extent of mutations as compared to PRRS virus strains found in previous outbreaks. Therefore, there exist needs to develop attenuated live vaccines which specifically target the virus strains causing the epidemic so as to effectively prevent the spread of PRRS.

SUMMARY OF THE INVENTION

In one aspect, the present disclosure provides an attenuated porcine reproductive and respiratory syndrome virus (PRRSV), comprising an RNA molecule encoded by a DNA polynucleotide, wherein the DNA polynucleotide encodes an Nsp2 protein and lacks a 360-nucleotide fragment, wherein the nucleotide fragment is at least about 70%, at least about 75%, at least about 80%, at least about 85%, at least about 90%, at least about 95%, at least about 96%, at least about 97%, at least about 98%, or at least about 99% homologous to SEQ ID NO: 7. In certain embodiments, the nucleotide fragment is SEQ ID NO: 7.

In certain embodiments, the present disclosure provides an attenuated porcine reproductive and respiratory syndrome virus (PRRSV), comprising an RNA molecule encoded by a DNA polynucleotide, wherein the DNA polynucleotide encodes an Nsp2 protein and the Nsp2 protein lacks a 120-amino acid fragment, wherein the amino acid fragment is at least about 70%, at least about 75%, at least about 80%, at least about 85%, at least about 90%, at least about 95%, at least about 96%, at least about 97%, at least about 98%, or at least about 99% homologous to SEQ ID NO: 6. In certain embodiments, the amino acid fragment is as shown in SEQ ID NO: 6. In certain embodiments, the Nsp2 protein has an amino acid sequence at least about 70%, at least about 75%, at least about 80%, at least about 85%, at least about 90%, at least about 95%, at least about 96%, at least about 97%, at least about 98%, or at least about 99% homologous to SEQ ID NO: 4. In certain embodiments, the Nsp2 protein has an amino acid sequence as shown in SEQ ID NO: 4.

In certain embodiments, the present disclosure provides an attenuated porcine reproductive and respiratory syndrome virus (PRRSV), comprising an RNA molecule encoded by a DNA polynucleotide, wherein the DNA polynucleotide encodes a Nsp2 protein and comprises a DNA sequence at least about 70%, at least about 75%, at least about 80%, at least about 85%, at least about 90%, at least about 95%, at least about 96%, at least about 97%, at least about 98%, or at least about 99% homologous to SEQ ID NO: 5. In certain embodiments, the DNA polynucleotide comprises a DNA sequence as shown in SEQ ID NO: 5.

In certain embodiments, the attenuated PRRSV provided herein is derived from serial passage of a parent PRRSV. In certain embodiments, the patent PRRSV is a PRRSV TJ staining having a deposit number of CGMCC2129 or having a genome sequence with GenBank Accession No. EU860248.

In certain embodiments, the present disclosure provides an attenuated PRRSV, comprising a PRRSV having a microorganism deposit number of CGMCC No. 3121.

In another aspect, the present disclosure provides a vaccine against PRRSV, wherein the vaccine comprises an attenuated PRRSV provided herein and a carrier acceptable for veterinary use.

In another aspect, the present disclosure provides an isolated polynucleotide comprising a DNA polynucleotide or a complement thereof, wherein the DNA polynucleotide encodes an Nsp2 protein of a PRRSV and lacks a 360-nucleotide fragment, wherein the 360-nucleotide fragment is at least about 70%, at least about 75%, at least about 80%, at least about 85%, at least about 90%, at least about 95%, at least about 96%, at least about 97%, at least about 98%, at least about 99%, or 100% homologous to SEQ ID NO: 7. In certain embodiments, the PRRSV is attenuated.

In certain embodiments, the present disclosure provides an isolated polynucleotide which encodes an attenuated PRRSV, comprising a DNA polynucleotide or a complement thereof, wherein the DNA polynucleotide encodes an Nsp2 protein of the attenuated PRRSV and lacks a 360-nucleotide fragment, wherein the 360-nucleotide fragment is at least about 70%, at least about 75%, at least about 80%, at least about 85%, at least about 90%, at least about 95%, at least about 96%, at least about 97%, at least about 98%, at least about 99%, or 100% homologous to SEQ ID NO: 7.

In another aspect, the present disclosure provides a vector comprising an isolated polynucleotide provided herein, and a host cell comprising the vector. In another aspect, the present disclosure provides a vaccine comprising the attenuated PRRSV provided herein, the isolated polynucleotide provided herein or the vector provided herein, and a carrier acceptable for veterinary use.

In another aspect, the present disclosure provides a method of preparing a vaccine against PRRSV comprising cultivating the attenuated PRRSV provided herein in a cell suitable for PRRSV growth and collecting the PRRSV. In certain embodiments, the cell suitable for PRRSV growth is Marc-145 cell.

In another aspect, the present disclosure provides a method of preventing a pig from infecting from a PRRSV or developing PRRS, comprising inoculating the pig with an attenuated PRRSV provided herein or a vaccine provided herein.

In another aspect, the present disclosure provides a method of characterizing PRRSV comprising the steps of collecting PRRSV of a sample and determining whether the PRRSV lacks a DNA sequence having at least about 80%, at least about 85%, at least about 90%, at least about 95%, at least about 96%, at least about 97%, at least about 98%, at least about 99% or 100% homology to SEQ ID NO: 7.

DETAILED DESCRIPTION OF THE INVENTION

Figure 1:
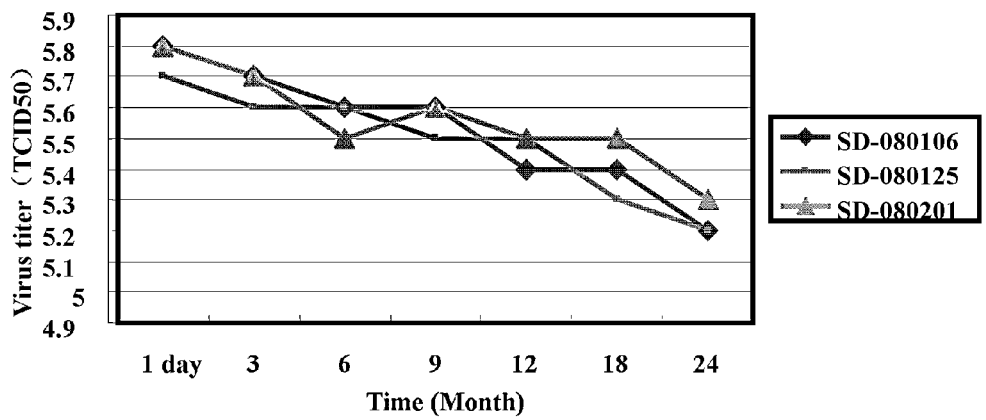
FIG. 1 shows the stability test results at 2-8° C. for the live vaccine of PRRSV.

The following description is merely intended to illustrate various embodiments of the present disclosure and such embodiments are not intended to be limiting. All references cited herein are incorporated herein by reference in their entirety.

One aspect of the present disclosure relates to attenuated porcine reproductive and respiratory syndrome viruses (PRRSV) which comprise an RNA molecule encoding an Nsp2 protein.

An "attenuated" PRRSV as used herein refers to a PRRSV which is capable of infecting and/or replicating in a susceptible host, but is non-pathogenic or less-pathogenic to the susceptible host. For example, the attenuated virus may cause no observable/detectable clinical manifestations, or less clinical manifestations, or less severe clinical manifestations, or exhibit a reduction in virus replication efficiency and/or infectivity, as compared with the related field isolated strains. The clinical manifestations of PRRSV infection can include, without limitation, fever, anorexia, labored respiration, cough, listlessness, lethargy, lymphadenopathy, gross and microscopic lesions in the lung, and reproductive failure characterized by delivery of weak or stillborn piglets, or autolysed fetuses. A "susceptible" host as used herein refers to a cell or an animal that can be infected by PRRSV. When introduced to a susceptible animal, an attenuated PRRSV may also induce an immunological response against the PRRSV or its antigen, and thereby render the animal immunity against PRRSV infection.

PRRSV is a type of virus containing a single-stranded positive sense RNA genome. The RNA genome of PRRSV comprises several open reading frames that encode proteins. Nsp2 protein is a non-structural protein encoded by a fragment of the first open reading frame of the PRRSV genome. The first open reading frame from the 5' end of the RNA genome of PRRSV is ORF1a, which encodes a polypeptide that is subsequently cleaved into several non-structural proteins known as Nsp1a, Nsp1b, Nsp2, Nsp3 and many others (see for details in: de Vries et al, Seminars in Virology, 8: 33-47 (1997); Allende et al, Journal of General Virology, 80: 307-315 (1999)). Nsp2 is one of the cleavage products and has a coding sequence in the RNA genome which is the third counting from the 5' end of ORF1a of PRRSV. Nsp2 is the single largest non-structural protein encoded by a fragment of ORF1a. The Nsp2 protein is believed to participate in the processing of the polypeptide encoded by ORF1a and formation of replication complex (Kim et al, Virus Genes, 38: 118-128 (2009)).

The RNA genome of PRRSV can be encoded by a DNA polynucleotide on the basis of Watson-Crick base pairing. The term "encodes", "encoded by", "encoding" or "encoding for" as used herein refers to being capable of being transcribed into an RNA sequence, and/or being capable of being translated into an amino acid sequence.

In certain embodiments, the present disclosure provides attenuated PRRSVs comprising an RNA molecule which can be encoded by a DNA polynucleotide, in which the DNA polynucleotide encodes an Nsp2 protein of PRRSV and lacks a 360-nucleotide fragment, in which the 360-nucleotide fragment is at least about 70%, at least about 75%, at least about 80%, at least about 85%, at least about 90%, at least about 95%, at least about 96%, at least about 97%, at least about 98%, or at least about 99% homologous to SEQ ID NO: 7. In certain embodiments, the 360-nucleotide fragment is SEQ ID NO: 7.

In order to identify the 360-nucleotide fragment lacking in the Nsp2 encoding sequence of a candidate PRRSV, the genetic sequence of the candidate PRRSV can be aligned with that of a reference PRRSV strain, and the sequence that is present in the Nsp2 encoding region of the reference strain but is absent in that of the candidate strain can be identified. Alignment of polynucleotide sequences can be performed using any suitable methods or softwares known in the art, such as for example, BLASTN (available from the website of National Center for Biotechnology Information (NCBI), also see, for example, Altschul S. F. et al, J. Mol. Biol., 215(3): 403-10 (1990)) and Clustal (available from the web site of European Bioinformatics Institute, see also, for example, Higgins D G et al, Methods in enzymology, 266: 383-402 (1996)). If the alignment of the sequences is performed using an appropriate software, the default parameters available in the software may be used, or otherwise the parameters may be customized to suit the alignment purpose.

In certain embodiments, the full genome sequence of the candidate PRRSV can be aligned with that of the reference PRRSV strain. In certain embodiments, the Nsp2 encoding sequence of the candidate PRRSV can be aligned with that of the reference PRRSV strain. The reference PRRSV strain can be a virulent strain which has a genome sequence sufficiently similar to that of the candidate PRRSV strain. In certain embodiments, the reference PRRSV strain is an American type PRRSV strain. In certain embodiments, the reference PRRSV strain can be the parent strain from which the candidate strain is derived. In certain embodiments, the reference PRRSV strain can be the PRRSV TJ strain having a genome sequence of GenBank Accession No. EU860248. After the sequence alignment, the sequence that is present in the Nsp2 encoding region of the reference strain but is absent in that of the candidate strain can be identified and further aligned with SEQ ID NO: 7 to determine the percent homology between the two sequences.

The term "percent (%) homologous to" with respect to polynucleotide sequences as used herein refers to the percentage of nucleotides in a candidate polynucleotide sequence that are identical to the nucleotides in a reference polynucleotide sequence, after aligning the candidate and the reference sequences and, if necessary, introducing gaps, to achieve the maximum number of identical nucleotides. The polynucleotide sequences can be aligned in various ways known in the art to determine the percent homology, for example, using publicly available computer softwares such as BLASTN and Clustal as described above. The percentage of homology of the candidate sequence to the reference sequence may be calculated as: 100 times the fraction X/Y, where X is the number of nucleotide scored as identical matches by the sequence alignment software in the alignment of the candidate sequence to the reference sequence, and where Y is the total number of the nucleotides in the reference sequence.

In certain embodiments, the absence of the 360-nucleotide fragment in the Nsp2 protein encoding region can render the PRRSVs attenuated. Without being bound to theory, but it is contemplated that such absence of the 360-nucleotide fragment can reduce the virulence of PRRSV by, for example, producing a non-functional or less-functional Nsp2 protein, and/or negatively affecting the expression or function of other PRRSV proteins, and/or negatively affecting the life cycle of the PRRSV.

In certain embodiments, the present disclosure provides an attenuated PRRSV, comprising an RNA molecule encoded by a DNA polynucleotide, wherein the DNA polynucleotide encodes an Nsp2 protein of PRRSV and comprises a nucleotide sequence at least about 70%, at least about 75%, at least about 80%, at least about 85%, at least about 90%, at least about 95%, at least about 96%, at least about 97%, at least about 98%, or at least about 99% homologous to shown in SEQ ID NO: 5. In certain embodiments, the DNA polynucleotide comprises a nucleotide sequence as shown in SEQ ID NO: 5.

In certain embodiments, the present disclosure provides an attenuated PRRSV, comprising an RNA molecule encoded by a DNA polynucleotide, wherein the DNA polynucleotide encodes a Nsp2 protein of PRRSV wherein the Nsp2 protein lacks a 120-amino acid fragment at least about 70%, at least about 75%, at least about 80%, at least about 85%, at least about 90%, at least about 95%, at least about 96%, at least about 97%, at least about 98%, or at least about 99% homologous to SEQ ID NO: 6. In certain embodiments, the Nsp2 protein lacks a 120-amino acid fragment which is SEQ ID NO: 6.

Similarly, the 120-amino acid fragment lacking in the Nsp2 protein sequence of a candidate PRRSV can be identified using a similar method as described above, i.e., by aligning the amino acid sequence of the Nsp2 protein of a candidate PRRSV strain against that of a reference PRRSV strain, and identifying the sequence that is present in the Nsp2 protein sequence of the reference strain but is absent in that of the candidate strain. Alignment of amino acid sequences can be performed using any suitable methods or softwares known in the art, such as for example, BLASTP (available from the website of National Center for Biotechnology Information (NCBI), see also, for example, Altschul S. F. et al, Nucl. Acids Res. 25: 3389-3402 (1997)), and Clustal (available from the website of European Bioinformatics Institute, see also, for example, Higgins D G, et al, Methods in enzymology, 266: 383-402 (1996)). If the alignment of the sequences is performed using an appropriate software, the default parameters available in the software may be used, or otherwise the parameters may be customized to suit the alignment purpose.

The reference PRRSV strain can be a virulent strain which has a genome sequence sufficiently similar to that of the candidate PRRSV strain. In certain embodiments, the reference PRRSV strain is an American type PRRSV strain. In certain embodiments, the reference PRRSV strain can be the parent strain from which the candidate strain is derived. In certain embodiments, the reference PRRSV strain can be the PRRSV TJ strain having a genome sequence of GenBank Accession No. EU860248. After the sequence alignment, the sequence that is present in the Nsp2 protein sequence of the reference strain but is absent in that of the candidate strain can be identified and further aligned with SEQ ID NO: 6 to determine the percent homology between the two sequences.

The term "percent (%) homologous to" with respect to amino acid sequences as used herein refers to the percentage of amino acid residues in a candidate amino acid sequence that are identical to the amino acid residues in a reference amino acid sequence, after aligning the sequences and, if necessary, introducing gaps, to achieve the maximum number of identical amino acids. Conservative substitution of the amino acid residues may be considered or may not considered as identical residues. "Conservative substitution" as used herein refers to replacing an amino acid residue with another amino acid residue that has similar physiochemical properties.

In certain embodiments, the Nsp2 protein of the attenuated PRRSV provided herein has an amino acid sequence at least about 70%, at least about 75%, at least about 80%, at least about 85%, at least about 90%, at least about 95%, at least about 96%, at least about 97%, at least about 98% or at least about 99% homologous to SEQ ID NO: 4. In certain embodiments, the Nsp2 protein of the attenuated PRRSV provided herein has an amino acid sequence as shown in SEQ ID NO: 4.

The attenuated PRRSVs provided herein can be derived by any suitable methods, for example, without limitation, by serial passage of a parent PRRSV, by introducing a recombinant vector encoding the PRRSV into a cell suitable for PRRSV growth and producing the PRRSV, or by isolating the virus from a sample containing the attenuated PRRSV.

In certain embodiments, the attenuated PRRSV provided herein is derived from serial passage of a PRRSV. The PRRSV from which the attenuated PRRSV is derived is the parent strain. The parent strain can be virulent. In certain embodiments, the parent strain can be serially passaged in a cell suitable for PRRSV growth. A "cell suitable for PRRSV growth" as used herein, refers to a type of cell that can produce virus particles of PRRSV after infection by a PRRSV, or after transfection with a polynucleotide encoding a PRRSV. In certain embodiments, the cell suitable for PRRSV growth used for serial passage is not a natural host for PRRSV. In certain embodiments, the cell suitable for PRRSV growth used for serial passage is not a porcine cell, such as for example, monkey cell (e.g. MA-104 cell, Marc-145 cell). During the serial passages, the virulence and/or the Nsp2 encoding sequence may be monitored, and PRRSV having reduced virulence as well as the deletion of the 360-nucleotide fragment may be selected.

In certain embodiments, the present disclosure provides attenuated PRRSV derived from a parent PRRSV strain—the PRRSV TJ strain—through serial passage. The PRRSV TJ strain is a highly virulent strain with a deposit number of CGMCC 2129, and its genome sequence has already been disclosed (GenBank Accession No. EU860248). PRRSV TJ strain is an American type PRRSV strain. When the Nsp2 protein encoded by the PRRSV TJ nucleotide is compared with that of the American type standard strain VR-2332 (the complete genome of which is disclosed in GenBank Accession No. AY150564), the Nsp2 protein of the TJ strain (CGMCC 2129 Nsp2) is found to contain a total deletion of 30 amino acids in VR-2332 Nsp2 protein, including deletions at the $481^{st}$ amino acid and from the $537^{th}$ to the $565^{th}$ amino acid of the Nsp2 sequence of VR-2332. The amino acid sequence of CGMCC 2129 Nsp2 is shown in SEQ ID NO: 2, which is encoded by the nucleotide sequence as shown in SEQ ID NO: 3.

In certain embodiments, the present disclosure provides an attenuated PRRSV strain TJM, with the following deposit information:
Microorganism Deposit Accession No.: CGMCC No. 3121;
Taxonomic Name: porcine reproductive and respiratory syndrome virus;
Deposit Address Institute for Microbiology, Chinese Academy of Sciences, No. 1 West Beichen Road, Chaoyang District, Beijing, China;
Deposit Center: China General Microbiological Culture Collection Center; and
Deposit Date: Jun. 15, 2009.
The PRRSV strain TJ has the following deposit information:
Microorganism Deposit Accession No.: CGMCC No. 2129;
Taxonomic Name: porcine reproductive and respiratory syndrome virus;
Deposit Address Institute for Microbiology, Chinese Academy of Sciences, No. 1 West Beichen Road, Chaoyang District, Beijing, China;
Deposit Center China General Microbiological Culture Collection Center; and
Deposit Date: Aug. 9, 2007.
The PRRSV TJM strain (Deposit No. CGMCC No. 3121) is resulted from attenuation of the PRRSV TJ strain. The PRRSV TJM strain is obtained by passaging the PRRSV TJ strain (Deposit No.: CGMCC NO. 2129) in cells and conducting plaque-purification every 10 passages to reduce the virulence of the PRRSV TJ strain.

The PRRSV TJM strain has an RNA molecule encoded by a DNA polynucleotide having a nucleotide sequence as shown in SEQ ID NO: 1. The Nsp2 protein of PRRSV TJM strain (CGMCC 3121 Nsp2) has an amino acid sequence as shown in SEQ ID NO: 4, which is encoded by the nucleotide sequence as shown in SEQ ID NO: 5. When CGMCC 3121 Nsp2 (SEQ ID NO: 4) is compared with CGMCC 2129 Nsp2 (SEQ ID NO: 2), the Nsp2 protein of TJM strain (SEQ ID NO: 4) is found to lack a fragment of continuous 120 amino acids (shown in SEQ ID NO: 6), ranging from the $598^{th}$ to the $717^{th}$ amino acid as shown in SEQ ID NO: 2. When the coding sequence (SEQ ID NO: 5) for CGMCC 3121 Nsp2 protein in the genomic nucleotide (SEQ ID NO: 1) is compared with the coding sequence (SEQ ID NO: 3) for CGMCC 2129 Nsp2 in the genomic nucleotide (Gene Bank Accession No. EU860248), the coding sequence (SEQ ID NO: 5) for CGMCC 3121 Nsp2 is found to lack a fragment of continuous 360 nucleotides (shown in SEQ ID NO: 7), ranging from the $1792^{nd}$ to the $2151^{st}$ nucleotide as shown in SEQ ID NO: 3. The sequence of the deleted or missing 120 amino acids is shown in SEQ ID NO: 6, and the corresponding nucleotide sequence is shown in SEQ ID NO: 7.

In certain embodiments, the attenuated PRRSV provided herein can be derived from recombination of a PRRSV encoding polynucleotide. For example, the 360-nucleotide fragment provided herein may be deleted from a PRRSV-encoding polynucleotide using recombinant methods such as restriction enzymes or PCR to produce a polynucleotide encoding the attenuated PRRSV provided herein. The resulted polynucleotide may be introduced into a cell suitable for PRRSV growth and produce the attenuated PRRSV by culturing the cell suitable for PRRSV growth.

Polynucleotides

Another aspect of the present disclosure relates to isolated polynucleotides comprising a DNA polynucleotide or any complement thereof, in which the DNA polynucleotide encodes an Nsp2 protein of PRRSV.

The term "polynucleotide" as used herein includes polyribonucleic acids (RNA), polydeoxyribonucleic acids (DNA), or mixed ribonucleic acids-deoxyribonucleic acids such as DNA-RNA hybrids. The polynucleotide may be single stranded or double-stranded. An "isolated polynucleotide" as used herein refers to a polynucleotide which is at least partially separated from the substances that associate with it in its natural state, if the polynucleotide indeed exists in a natural state in nature.

As used herein, a "complement" of a polynucleotide (the first polynucleotide) refers to a second polynucleotide which is non-identical to the first polynucleotide but either has a complementary base sequence to the first polynucleotide, or encodes the same amino acid sequence as the first polynucleotide.

A complement of a first DNA polynucleotide may include, without limitation: 1) a second DNA polynucleotide complementary to the first DNA polynucleotide; 2) a second RNA polynucleotide encoding the same amino acid sequence as the first DNA polynucleotide; 3) a second DNA polynucleotide encoding the same amino acid sequence as the first DNA polynucleotide, but containing one or more degenerate codon. Degenerate codons are different triplets of nucleotides which encode for the same amino acid.

A complement of a first RNA polynucleotide may include, without limitation: 1) a DNA polynucleotide complementary to the first RNA polynucleotide; and 2) a DNA polynucleotide encoding the same amino acid sequence as the RNA polynucleotide.

In certain embodiments, the present disclosure provides isolated polynucleotides comprising a DNA polynucleotide or any complement thereof, wherein the DNA polynucleotide encodes an Nsp2 protein of PRRSV, wherein the Nsp2 protein lacks a 120-amino acid fragment at least about 70%, at least about 75%, at least about 80%, at least about 85%, at least about 90%, at least about 95%, at least about 96%, at least about 97%, at least about 98%, or at least about 99% homologous to SEQ ID NO: 6. In certain embodiments, the 120-amino acid fragment is as shown in SEQ ID NO: 6. In certain embodiments, the Nsp2 protein of PRRSV has an amino acid sequence at least about 70%, at least about 75%, at least about 80%, at least about 85%, at least about 90%, at least about 95%, at least about 96%, at least about 97%, at least about 98%, or at least about 99% homologous to SEQ ID NO: 4. In certain embodiments, the Nsp2 protein has an amino acid sequence as shown in SEQ ID NO: 4.

In certain embodiments, the present disclosure provides isolated polynucleotides comprising a DNA polynucleotide or any complement thereof, wherein the DNA polynucleotide encodes an Nsp2 protein of PRRSV and lacks a 360-nucleotide fragment at least about 70%, at least about 75%, at least about 80%, at least about 85%, at least about 90%, at least about 95%, at least about 96%, at least about 97%, at least about 98%, or at least about 99% homologous to SEQ ID NO:

7. In certain embodiments, the 360-nucleotide fragment is as shown in SEQ ID NO: 7. In certain embodiments, the DNA polynucleotide encodes an Nsp2 protein of PRRSV and comprises a nucleotide sequence at least about 70%, at least about 75%, at least about 80%, at least about 85%, at least about 90%, at least about 95%, at least about 96%, at least about 97%, at least about 98%, or at least about 99% homologous to SEQ ID NO: 5. In certain embodiments, the DNA polynucleotide comprises a nucleotide sequence as shown in SEQ ID NO: 5.

In certain embodiments, the present disclosure provides isolated polynucleotides comprising a DNA polynucleotide encoding an attenuated PRRSV or any complement thereof, in which the DNA polynucleotide encodes an Nsp2 protein of the PRRSV and the Nsp2 protein lacks a 120-amino acid fragment as provided herein. In certain embodiments, the DNA polynucleotide encodes an Nsp2 protein of the PRRSV and the Nsp2 protein has an amino acid sequence as provided herein.

In certain embodiments, the present disclosure provides isolated polynucleotides comprising a DNA polynucleotide encoding an attenuated PRRSV or any complement thereof, wherein the DNA polynucleotide lacks a 360-nucleotide fragment as provided herein. In certain embodiments, the DNA polynucleotide encodes an Nsp2 protein of the PRRSV and has a nucleotide sequence as provided herein.

Vector and Host Cells

In another aspect, the present disclosure provides vectors comprising an isolated polynucleotide provided herein. A "vector" as used herein refers to a carrier that can deliver a target polynucleotide into a host cell. After transporting into the cell, the target polynucleotide may get transcribed into RNA molecules, or be translated into proteins, or replicate as the vector replicates in the host cell. Examples of suitable vectors include, without limitation, plasmids and viral vectors.

In certain embodiments, the vector is a plasmid. The plasmid vector can contain an isolated polynucleotide provided herein, as well as other necessary elements such as a replication origin which is useful for replication of the vector, and a RNA polymerase promoter which is useful for transcription and/or expression of the polynucleotide contained therein. The plasmids may optionally contain a marker gene for selection. In certain embodiments, plasmid vectors which contain an isolated polynucleotide encoding an attenuated PRRSV as provided herein are useful in producing an attenuated PRRSV in a host cell.

In certain embodiments, the vector is a viral vector containing a polynucleotide provided herein. The viral vectors are useful in infecting a host cell and thereby deliver the polynucleotide contained therein into the cell. The viral vectors may be based on RNA virus or DNA virus. Any suitable viral vectors may be used, such as virus vectors based on swine viruses, or virus vectors based on other viruses such as mammalian viruses and avian viruses.

In certain embodiments, the present disclosure provides host cells containing a vector provided herein. The term "host cell" used herein refers to a cell into which the vector can be introduced, for example, by transduction, transfection, electroporation, infection, or cell fusion. In certain embodiments, the host cell can support the replication and/or the expression of the vector. Suitable host cells for the purpose of the present disclosure can include, without limitation, bacteria cells such as E. Coli, fungal cells, insect cells, mammalian cells, and avian cells.

The host cells can be used to isolate the vectors contained therein, or can be cultured under suitable conditions to allow replication of the vectors, production of RNA molecules encoding a PRRSV, and/or production of virus particles of PRRSV.

Vaccines Against PRRSV

In another aspect, the present disclosure provides vaccines against PRRSV. The vaccines can comprise the attenuated PRRSVs provided herein, the isolated polynucleotides provided herein, or the vectors provided herein.

In certain embodiments, the vaccines comprise an attenuated PRRSV comprising a RNA molecule which can be encoded by a DNA polynucleotide, in which the DNA polynucleotide encodes an Nsp2 protein of PRRSV and lacks a 360-nucleotide fragment as provided herein. In certain embodiments, the DNA polynucleotide encodes an Nsp2 protein of PRRSV and comprises a nucleotide sequence as provided herein.

In certain embodiments, the vaccines comprise an attenuated PRRSV comprising a RNA molecule which can be encoded by a DNA polynucleotide, in which the DNA polynucleotide encodes an Nsp2 protein of the PRRSV and the Nsp2 protein lacks a 120-amino acid fragment as provided herein. In certain embodiments, the DNA polynucleotide encodes an Nsp2 protein of the PRRSV and the Nsp2 protein has an amino acid sequence as provided herein.

In certain embodiments, the present disclosure provides a vaccine comprising an attenuated PRRSV which is PRRSV TIM strain, with a Deposit No. of CGMCC No. 3121.

In certain embodiments, the present disclosure provides a vaccine comprising a polynucleotide or any complement thereof, as provided herein.

In certain embodiments the present disclosure provides a vaccine comprising a vector, wherein the vector comprises an isolated polynucleotide encoding an attenuated PRRSV as provided herein.

In certain embodiments, the vaccines provided herein further comprise a carrier suitable for veterinary use. A "carrier" as used herein refers to any vehicle or composition that is involved in delivery of vaccine into the subject or that facilitates the storage of the vaccine. In certain embodiments, the carrier is suitable for delivery and/or storage of vaccines containing polynucleotide. In certain embodiments, the carrier is suitable for delivery and/or storage of vaccines containing attenuated PRRSV, the vector, or the isolated polynucleotide. Carriers suitable for the purpose of the present disclosure can include water, buffers, saline, liposomes, polymeric materials, preservatives, oils, emulsions, preservatives, stabilizers and/or carrier particles, and can be selected by persons having ordinary skills in the art as needed.

In certain embodiments, the vaccines provided herein can further comprise a cryoprotectant. A "cryoprotectant" as used herein refers to a substance that can help stabilize a biological material during freezing process and thereby prevent significant loss of activity of the biological material due to freezing damages. Suitable cryoprotectants for vaccines include, without limitation, dimethyl sulfoxide, glycerol, lactose, glutamic acid, sodium glutamate, lactic acid, glucose, sorbitol, histamine, albumin, and gelatin.

In certain embodiments, the cryoprotectant is heat-resistant. Suitable heat-resistant cryoprotectant include, without limitation, sucrose, L-sodium glutamate, N-Z, lactalbumin hydrolysate, gelatin, fucose, and polyvinylpyrrolidone. In certain embodiments, the vaccine comprises a heat-resistant cryoprotectant which comprises 10-30% sucrose (w/v), 0.01-5% L-sodium glutamate (w/v), 0.1-10% N-Z (w/v), 10-30% lactalbumin hydrolysate (w/v), and 0.1-10% gelatin (w/v). In certain embodiments, the heat-resistance cryoprotectant can be prepared by mixing and dissolving 10-30% sucrose (w/v), 0.01-5% L-sodium glutamate (w/v), 0.1-10% N-Z (w/v), 10-30% lactalbumin hydrolysate (w/v), and 0.1-10% gelatin (w/v), and autoclaving the mixture to obtain said heat-resistant cryoprotectant.

Preparation Methods

In another aspect, the present disclosure further provides methods of preparing a vaccine provided herein, comprising producing an attenuated PRRSV in a cell suitable for PRRSV growth.

The cell suitable for PRRSV growth can include, without limitation, monkey cells such as MA-104 cells and Marc-145 cells, and porcine alveolar macrophage cells. In certain embodiments, the cell suitable for PRRSV growth is Marc-145 cells.

In certain embodiments, the cells suitable for PRRSV growth can be prepared using any of the following methods:
1) cultivating the cells useful for PRRSV growth in roller bottles to allow the cells to reach a cell density of $5\text{-}10\times10^7$/ml; or
2) cultivating the cell suitable for PRRSV growth in suspension culture, optionally with microcarriers, to allow the cells to reach a cell density of $5\text{-}10\times10^7$/ml-$5\text{-}10\times10^8$/ml.

In certain embodiments, the present disclosure provides methods of preparing a vaccine provided herein, comprising introducing a polynucleotide encoding an attenuated PRRSV as provided herein into a cell suitable for PRRSV growth, culturing the cell and collecting the PRRSV.

In certain embodiments, the present disclosure provides methods of preparing a vaccine provided herein, comprising introducing a vector encoding an attenuated PRRSV as provided herein into a cell suitable for PRRSV growth, culturing the cell and collecting the PRRSV. The attenuated PRRSV may be collected from the supernatant of the cell culture or from the cell lysate, using conventional separation and/or purification methods such as centrifugation.

In certain embodiments, the present disclosure provides methods of preparing a vaccine provided herein, comprising cultivating an attenuated PRRSV as provided herein in a cell suitable for PRRSV growth and collecting the PRRSV. In certain embodiments, the step of cultivating the PRRSV in a cell suitable for PRRSV growth further comprises inoculating the PRRSV at a multiplicity of infection (MOI) of 0.01-0.5 onto the cell suitable for PRRSV growth.

In certain embodiments, the step of collecting the PRRSV further comprises collecting virus fluid after cultivation for 3-5 days when the cytopathic effects reach 70%.

In certain embodiments, the methods for preparing a vaccine provided herein further comprise mixing the collected PRRSV with a heat-resistant cryoprotectant. In certain embodiments, the methods for preparing a vaccine provided herein further comprise filling a predetermined amount of the mixture of the PRRSV and the heat-resistant cryoprotectant into an ampoule, and freeze-drying the mixture.

In certain embodiments, the present disclosure provides methods of preparing a vaccine provided herein, comprising steps of cultivating PRRSV TJM strain (Microorganism Deposit No.: CGMCC NO. 3121) in cells suitable for PRRSV growth and collecting the virus fluid. The methods further comprises a step of providing a heat-resistant cryoprotectant and mixing the virus fluid and the heat-resistant cryoprotectant into a mixture. The methods further comprising steps of filling a predetermined amount of the mixture into an ampoule and freeze-drying the vaccine after the ampoule is capped and placed in a freeze-dryer for pre-freeze and drying.

In certain embodiments, the mixture of the virus fluid and the heat-resistant cryoprotectant herein comprises 6-8 portions (v/v) of the virus fluid and 2-4 portions (v/v) of the cryoprotectant.

Method of Use

In certain embodiments, the present disclosure provides a method of preventing a pig from infecting from a PRRSV or developing PRRS, comprising inoculating the pig with the attenuated PRRSV provided herein, or the vaccine provided herein. The vaccines can be inoculated via any suitable administration route, including without limitation, intramuscular, intranasal, intratracheal, oral, and parental routes. The vaccines can be inoculated at a suitable dosage that can render effective protection to the vaccinated pigs without causing significant adverse effects.

In certain embodiments, the present disclosure provides a method of characterizing PRRSV comprising the steps of colleting PRRSV of a sample and determining whether the PRRSV lacks a polynucleotide encoded by a DNA polynucleotide having at least about 90% homology to SEQ ID NO: 7.

In certain embodiments, the present disclosure provides uses of the polynucleotides provided herein. In certain embodiments, the polynucleotides of the present disclosure can be used to distinguish the PRRSV vaccine strains that lack the 360-nucleotide fragment/region provided herein, from other PRRSV strains that contain such fragment/region. For example, the polynucleotides of the present disclosure can be used to design primers that are corresponding to the region, which primers can then be used in PCR reactions using virus-containing samples as the templates, for detection of the presence or absence of the 360-nucleotide region in the templates or strains.

In certain embodiments, the polynucleotides of the present disclosure can be used in diagnosis of PRRSV infection, in which pigs infected with a field strain of PRRSV can be distinguished from pigs vaccinated with any of the vaccines provided herein. In certain embodiments, the polynucleotides of the present disclosure can be used in quality control of the vaccines provided herein, in which vaccines contaminated with a field strain can be distinguished.

Advantages

The present disclosure provides vaccines comprising polynucleotides encoding an attenuated PRRSV as well as vaccines comprising an attenuated PRRSV. Compared with an inactivated vaccine, an attenuated vaccine can offer great advantages in activating immune responses in a host. First, as a live replicating virus in the host, the attenuated vaccine strain can be readily detected by the immune system, and thereby can activate a wide spectrum of immune responses. Second, since attenuated vaccine strain can replicate in host, they continuously present antigens to the immune system and therefore provides durable immunity and requires less often vaccination or boosters.

The attenuated vaccine strain and the formulations thereof provided in the present disclosure demonstrate significant technical effects in the prevention of PRRS. The attenuated vaccine strain does not show return of virulence after 5 passages in inoculated animals, thereby effectively solving the problem of virulence return. The safety study results shows that, after either a single dose inoculation, repetitive single dose inoculations, or a 10-fold high dose inoculation, the inoculated pigs maintain normal body temperatures without any signs of clinical symptoms, and the biopsy observation show no pulmonary polypoid lesion. These indicate that the live attenuated vaccine of PRRSV is safe to pigs. The vaccine efficacy study shows that the vaccine of the present disclosure can provide effective protection against challenge of virulent strains, and can effectively prevent the pigs from developing porcine reproductive and respiratory syndrome. The immune duration study of the vaccine shows that the immune duration period lasts for 4 months, within which period the vaccine can provide effective protection to pigs. The stability test of the vaccine shows that the vaccine can be stored for 24 months at 2-8° C.

EXAMPLES

The following examples are intended to further describe the inventions together with the figures. However, these descriptions should not be construed to constitute limitations to the scope of the present disclosure. The scope of the present invention should be determined by the claims.

Example 1

Attenuation of PRRSV TJ Strain by Serial Passages

A PRRSV strain was isolated from a pathological sample collected from a diseased dead pig in a pig farm which had an outbreak of high fever disease in Tianjin, China. The strain was named as PRRSV TJ strain, and the GeneBank Accession number of the virus strain is EU860248. The virus strain was deposited under a Microorganism Deposit No. of CGMCC NO. 2129. The full length genome of PRRSV TJ strain was 15324 bp (including Poly A tail). The Nsp2 sequence of TJ strain contained a deletion at the $481^{st}$ amino acid and deletions from the $532^{rd}$ to the $560^{th}$ amino acid, when compared with that of the American type standard virus strain VR-2332. The Nsp2 sequences of the two strains shared 83.7% identity in nucleotide sequence and 77.9% identity in the encoded amino acid sequence. The study results showed that, the isolated strain was a mutated PRRSV which was highly-virulent to pigs. The PRRSV TJ strain was passaged serially in Marc-145 cells, and purified through plaque purification every 10 passages. When the virus strain is passaged to the F92 passage, the whole genome sequence of the obtained virus strain was amplified and the virus was studied for its virulence. The results demonstrated that the PRRSV TJ strain at the F92 passage was safe to experimental animals and was therefore named as PRRSV TJM strain for live vaccine study.

Example 2

Study for Return of Virulence of PRRSV TJM Strain

PRRSV TJM strain was attenuated from virulent high fever disease virus (PRRSV TJ strain), and was characterized and stored. The study further tested whether the vaccine strain had potentials in return of virulence. In the $1^{st}$ test for return of virulence, PRRSV TJM strain was inoculated to 4-week old healthy piglets negative for PRRS, via intramuscular injection into neck muscle at a dose of 2 ml per piglet, $10^{5.7}$TCID$_{50}$/ml. Piglets without any inoculation were kept as negative controls. In the $2^{nd}$ test through the $5^{th}$ test for return of virulence, the PRRSV positive serums obtained from piglets in the previous test were combined and used as the inoculum for piglets in the next test for return of virulence. In each test, piglets were inoculated via intramuscular injection into neck muscle, and piglets without any inoculation were kept as negative controls. After each inoculation, rectal temperatures of the experimental animals were taken at a regular time point for 14 consecutive days, and animals were observed for clinical signs for 14 days. Blood samples were taken every other day to detect viral presence in serum, which serum can be used as inoculum for the next test of virulence return. In the $5^{th}$ test for return of virulence, the experimental animals were observed for 21 days after the inoculation. Starting from the $2^{nd}$ test, the virus inoculum could no longer be expanded in in vitro cultures. The inoculated animals showed normal body temperatures in the 5 studies, and demonstrated no clinical signs of disease onset. The results showed that, when the PRRSV TJM strain was introduced back to susceptible animals, it did not cause any disease onset in the experimental animals after 5 tests for return of virulence, which indicated the virus strain did not return virulent after 5 passages, and therefore could be used in vaccine studies.

Example 3

Genetic Analysis of Mutations in PRRSV TJM Strain

PRRSV TJ strain was attenuated into PRRSV TJM strain by serial passaging of the virus in Marc-145 cells. The Nsp2 gene of the PRRSV TJM strain was sequenced, and the sequence was compared with that of PRRSV TJ strain and that of the American type standard PRRSV VR-2332 strain. The results showed that, the Nsp2 gene of PRRSV TJM strain had a full length of 2490 bp, and shared a nucleotide sequence identity of 98.6% and 82.9%, respectively, with that of PRRSV TJ strain and that of American type standard virus strain VR-2332; and an amino acid sequence identity of 97.6% and 75.8%, respectively, with that of PRRSV TJ strain and that of American type standard virus strain VR-2332. When compared with the Nsp2 sequence of PRRSV TJ strain, the sequence of TJM strain contained a continuous deletion of 120 amino acids from the $598^{th}$ to the $717^{th}$ amino acid; when compared with the Nsp2 sequence of VR-2332 strain, the sequence of TJM strain contained a total deletion of 150 amino acids including deletions of the $481^{st}$ amino acid, from the $537^{th}$ to the $565^{th}$ amino acid and from the $628^{th}$ to the $747^{th}$ amino acid. The nucleotide sequence of PRRSV TJM strain is shown in SEQ ID NO: 1.

Example 4

Preparation of Live Vaccines for Porcine Reproductive and Respiratory Syndrome

1. Preparation of virus fluid for vaccine preparation. PRRSV TJM strain was inoculated at a multiplicity of infection (MOI) of 0.01-0.5 to confluent single layer of Marc-145 cells, maintenance fluid was added and the cells were cultured in roller culture apparatus. Virus fluid was collected when cytopathic effects (CPE) were above 70%. After two cycles of freeze and thaw, the virus titer (TCID$_{50}$) was determined, and samples were tested for sterility, mycoplasma, and exogenous virus.

2. Preparation of heat-resistance cryoprotectant. 10-30% sucrose (w/v), 0.01-5% L-sodium glutamate (w/v), 0.1-10% N-Z (w/v), 10-30% lactalbumin hydrolysate (w/v), and 0.1-10% gelatin (w/v) were mixed and dissolved, followed by autoclave, for later use.

3. 5-8 portions (v/v) of the virus fluid and 2-5 portions (v/v) of the cryoprotectant were mixed even, split into predetermined amounts and filled into ampoules. The ampoules were capped and placed in a freeze-dryer for freeze-drying the vaccine after pre-freeze and drying processes. The freeze-dried vaccines were tested for sterility, safety and efficacy.

Example 5

Safety Study of the Live Vaccine of PRRSV 3 batches of lab-made vaccines were tested for safety according to the following procedures.

The 3 batches of lab-made live vaccines for PRRSV were inoculated to 4-5 week old healthy piglets negative for PRRS, via intramuscular injection into neck muscle. Each group of piglets received single dose inoculation, repetitive single dose inoculations, or 10-fold high dose inoculation, respectively, at a dose of $10^{5.0}TCID_{50}$/ml/dose. Each group had 15 piglets, and 5 non-inoculated piglets were also kept as negative controls. After the inoculations, rectal temperatures of the experimental animals were taken at a regular time point everyday for 14 consecutive days, and animals were observed for clinical symptoms. Experimental animals were dissected 21 days after the inoculation to observe for any lesions in lungs. The results of the study showed that, after either a single dose inoculation, repetitive single dose inoculations, or 10-fold high dose inoculation, the inoculated pigs maintained normal body temperatures without any signs of clinical symptoms, and the biopsy observation showed no pulmonary polypoid lesion, which indicated the live vaccine of PRRSV was safe to pigs.

Example 5

Efficacy Study of the Live Vaccine of PRRSV 3 batches of lab-made live vaccines of PRRSV were used to inoculate 3-5 week old healthy weaned piglets negative for PRRS. The piglets were divided into 4 groups, each having 5 piglets.

Piglets in the first group through the third group (immunization groups) were inoculated with the 3 batches of lab-made live vaccines of PRRSV, respectively, at a dose of 1 dose per piglet, $10^{5.0}TCID_{50}$/dose/ml, via intramuscular injection into neck muscle.

The fourth group was the control group, which was inoculated with 1 ml control cell culture medium of Marc-145 cells.

After the immunization, animals were observed for clinical reactions and adverse effects of the vaccines. Blood samples were taken each week, and serums were isolated for detection of serum antibodies. Animals were weighed each week.

4 weeks after the immunization, the animals in the four study groups were challenged with a 50-fold diluted virulent strain PRRSV TJ strain (having a potency of $10^{5.8}TCID_{50}$/ml) at a challenge dose of 2 ml virus fluid per piglet. The virus fluid was inoculated intranasally at 1 ml in each nostril. After inoculation of the virulent strain, the animals were observed each day for clinical symptoms, including appetite, spirit, etc. Rectal temperatures were taken everyday, blood samples were taken every two days and serums were isolated for virus isolation and characterization. The study ended 21 days after the virus challenge.

Results of the study:

1. After the inoculation of the vaccine, the experimental animals showed normal body temperatures, and no clinical symptoms were observed. The weight increases in vaccine inoculation group and the control group did not show any significant difference.

2. After the virus challenge, the vaccine-inoculated group showed a protection rate of 4/5, whereas the control group had 5 out of 5 piglets demonstrating disease onset, among which 2 out of 5 piglets died.

The study results showed, the vaccine of the present disclosure provided good protection against challenge of virulent strains, and effectively prevented infection of PRRSV.

Example 7

Immune Duration Study of Live Vaccine of PRRSV 3 batches of lab-made live vaccines of PRRSV were diluted with phosphate buffered saline (PBS) to $10^{5.0}TCID_{50}$/ml. The vaccines were inoculated to 4-5 week old healthy weaned piglets negative for PRRS, via intramuscular injection into neck muscle at a dose of 1 ml per piglet, for determination of the immune duration period. Piglets in inoculated groups and the control group were picked for virus challenge study at 2 months, 4 months or 6 months after the inoculation of vaccines, respectively. The results showed that, when experimental animals were challenged with virus at 2 months after the vaccine inoculation, no animals died in groups inoculated with the 3 batches of vaccines, and the protection rate reached 4/5. When challenged with virus at 4 months after the vaccine inoculation, no animals died in groups inoculated with the 3 batches of vaccines, and the protection rate reached 4/5. When challenged with virus at 6 months after the vaccine inoculation, no animals died in groups inoculated with the 3 batches of vaccines, and the protection rate reached above 3/5. Therefore, the immune duration period was determined as 4 months, to make sure the vaccine provides effective protection to pigs within the immune duration period.

Example 8

Stability Test of the Live Vaccine of PRRSV

Figure 2:
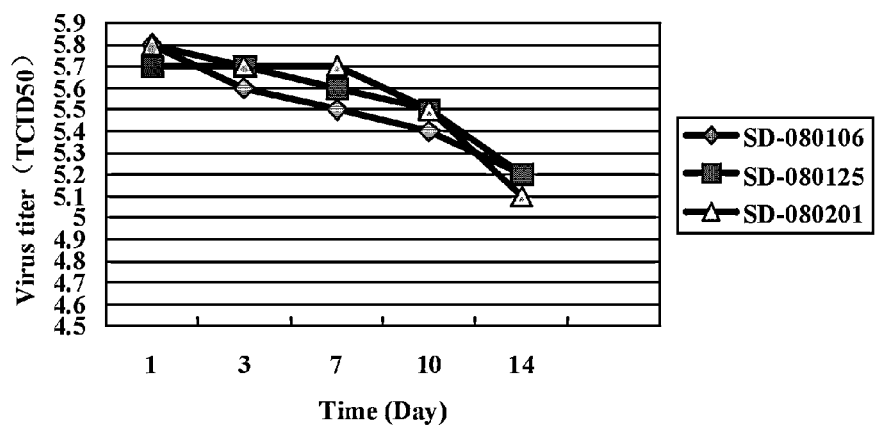
FIG. 2 shows the aging resistance study results of the PRRSV vaccine at 37° C.

The 3 batches (080106, 080125 and 080201) of preparations of the lab-made live vaccines (antigen contents were $10^{5.8}TCID_{50}$/ml/dose, $10^{5.7}TCID_{50}$/ml dose, $10^{5.8}TCID_{50}$/ml/dose) were stored between 2-8° C. for 3, 6, 9, 12, 18, 24, 30, and 40 months. Samples were taken and tested for characteristics, vacuum degree, water content, efficacy (see FIG. 1) and aging resistance at 37° C. (see FIG. 2). Results: after storage at 2-8° C. for 24 months, the 3 batches of preparations remained white loose lumps which dissolved quickly at the addition of a diluting solution. The average residual water content was within the required range. The preparations showed white or purple glow in vacuum degree measurement. The antigen contents in the preparations were $10^{5.2}TCID_{50}$/ml/dose, $10^{5.2}TCID_{50}$/ml/dose, and $10^{5.3}TCID_{50}$/ml/dose, respectively. After storage at 37° C. for 14 days, the antigen contents were $10^{5.2}TCID_{50}$/ml/dose, $10^{5.2}TCID_{50}$/ml/dose, and $10^{5.1}TCID_{50}$/ml/dose, respectively, which were still above the required content ($10^{5.2}TCID_{50}$/ml/dose) for freeze-dried vaccines. Therefore, the shelf life of the vaccine was 24 months.

We claim:

1. An attenuated porcine reproductive and respiratory syndrome virus (PRRSV), comprising an RNA molecule encoded by a DNA polynucleotide, wherein the DNA polynucleotide encodes an Nsp2 protein, wherein the Nsp2 protein lacks a 120-amino acid region encoded by a 360-nucleotide fragment, wherein the fragment is at least about 80% homologous to SEQ ID NO: 7.

2. The attenuated PRRSV of claim 1, wherein the fragment is at least about 85% homologous to SEQ ID NO: 7.

3. The attenuated PRRSV of claim 1, wherein the fragment is at least about 90% homologous to SEQ ID NO: 7.

4. The attenuated PRRSV of claim 1, wherein the fragment is at least about 95% homologous to SEQ ID NO: 7.

5. The attenuated PRRSV of claim 1, wherein the fragment is SEQ ID NO: 7.

6. The attenuated PRRSV of claim 1, wherein the fragment encodes a 120-amino acid fragment as shown in SEQ ID NO: 6.

7. The attenuated PRRSV of claim 1, wherein the Nsp2 protein has an amino acid sequence as shown in SEQ ID NO: 4.

8. The attenuated PRRSV of claim 1, wherein the DNA polynucleotide has a DNA sequence as shown in SEQ ID NO: 5.

9. The attenuated PRRSV of claim 1, wherein the PRRSV is derived from serial passage of a parent PRRSV.

10. The attenuated PRRSV of claim 9, wherein the parent PRRSV has a microorganism deposit number of CGMCC No. 2129.

11. The attenuated PRRSV of claim 1, wherein the PRRSV has a microorganism deposit number of CGMCC No. 3121.

12. A vaccine against PRRSV, wherein the vaccine comprises an attenuated PRRSV of claim 1.

13. The vaccine of claim 12, further comprising a carrier acceptable for veterinary use.

14. The vaccine of claim 13, further comprising a heat-resistant cryoprotectant.

15. The vaccine of claim 14, wherein the heat-resistant cryoprotectant comprises 10-30% sucrose (w/v), 0.01-5% L-sodium glutamate (w/v), 0.1-10% N-Z (w/v), 10-30% lactalbumin hydrolysate (w/v), and 0.1-10% gelatin (w/v).

16. A method of preventing a pig from infection from a PRRSV or developing PRRS, comprising inoculating the pig with the attenuated PRRSV of claim 1.

17. A method of preventing a pig from infection from a PRRSV or developing PRRS, comprising inoculating the pig with the vaccine of claim 12.

* * * * *